United States Patent
Hebert et al.

(10) Patent No.: US 6,900,777 B1
(45) Date of Patent: May 31, 2005

(54) INFRARED AUDIO/VIDEO INTERFACE FOR HEAD-MOUNTED DISPLAY

(75) Inventors: Raymond T. Hebert, Los Gatos, CA (US); Kevin R. Hempson, Los Gatos, CA (US)

(73) Assignee: Stryker Corporation, Kalamazoo, MI (US)

( * ) Notice: Subject to any disclaimer, the term of this patent is extended or adjusted under 35 U.S.C. 154(b) by 379 days.

(21) Appl. No.: 09/756,648

(22) Filed: Jan. 3, 2001

(51) Int. Cl.[7] .................................................. G09G 5/00
(52) U.S. Cl. .............................. 345/7; 345/30; 345/8; 359/618
(58) Field of Search .......................... 345/7, 8, 9, 30, 345/59; 359/618, 709, 717, 646, 630; 349/11; 385/33, 35

(56) References Cited

U.S. PATENT DOCUMENTS

| | | | | |
|---|---|---|---|---|
| 3,674,925 A | * | 7/1972 | Heckman, Jr. ............... 178/6.8 |
| 5,005,213 A | * | 4/1991 | Hanson et al. .............. 455/617 |
| 5,579,026 A | * | 11/1996 | Tabata ........................... 345/8 |
| 5,619,183 A | * | 4/1997 | Ziegra et al. ............... 340/505 |
| 5,671,158 A | * | 9/1997 | Fournier et al. ......... 364/514 R |
| 5,710,671 A | | 1/1998 | Bichlmaier ................. 359/742 |
| 5,745,519 A | * | 4/1998 | Ruda et al. ................. 372/101 |
| 6,005,633 A | * | 12/1999 | Kosugi ....................... 348/518 |
| 6,008,939 A | * | 12/1999 | Hebert ....................... 359/475 |
| 6,028,708 A | * | 2/2000 | Gramann et al. ........... 359/629 |
| 6,046,712 A | * | 4/2000 | Beller et al. .................... 345/8 |
| 6,101,038 A | * | 8/2000 | Hebert et al. ............... 359/618 |
| 6,154,300 A | * | 11/2000 | Cho ............................ 398/126 |
| 6,342,915 B1 | * | 1/2002 | Ozaki et al. .................. 348/61 |
| 6,430,433 B1 | * | 8/2002 | Luber et al. ................ 600/425 |
| 6,483,483 B2 | * | 11/2002 | Kosugi et al. .................. 345/8 |

FOREIGN PATENT DOCUMENTS

DE             3916121         11/1989

* cited by examiner

Primary Examiner—Regina Liang
Assistant Examiner—Jennifer T. Nguyen
(74) Attorney, Agent, or Firm—Winston & Strawn LLP

(57) ABSTRACT

A video interface linking a base station with a remote display, e.g., a head-mounted display, converts input video signals from NTSC or PAL formats into modulated video signals containing repetitive sequences of frame times with embedded audio and control signals. Each frame time includes equal consecutive color field times. Frame rates are converted by inserting selected repeating color frames into the datastream. Bursts of image information occupy a portion of each field time. During each data burst, the display is loaded with pixel luminance data. Between bursts, the display is illuminated by a color LED. Two video displays can be driven alternately, i.e., the first display loads while the second is illuminated. The modulated video signal can travel through the atmosphere on an infrared (IR) beam with a wavelength between 700 nm and 1100 nm. In one embodiment, the beam is scattered from a diffuse reflecting surface. Alternatively, the beam is emitted from an array of infrared light emitting diodes (LEDs). Designs for collecting lens assemblies are described. Some embodiments include return audio transmission.

52 Claims, 14 Drawing Sheets

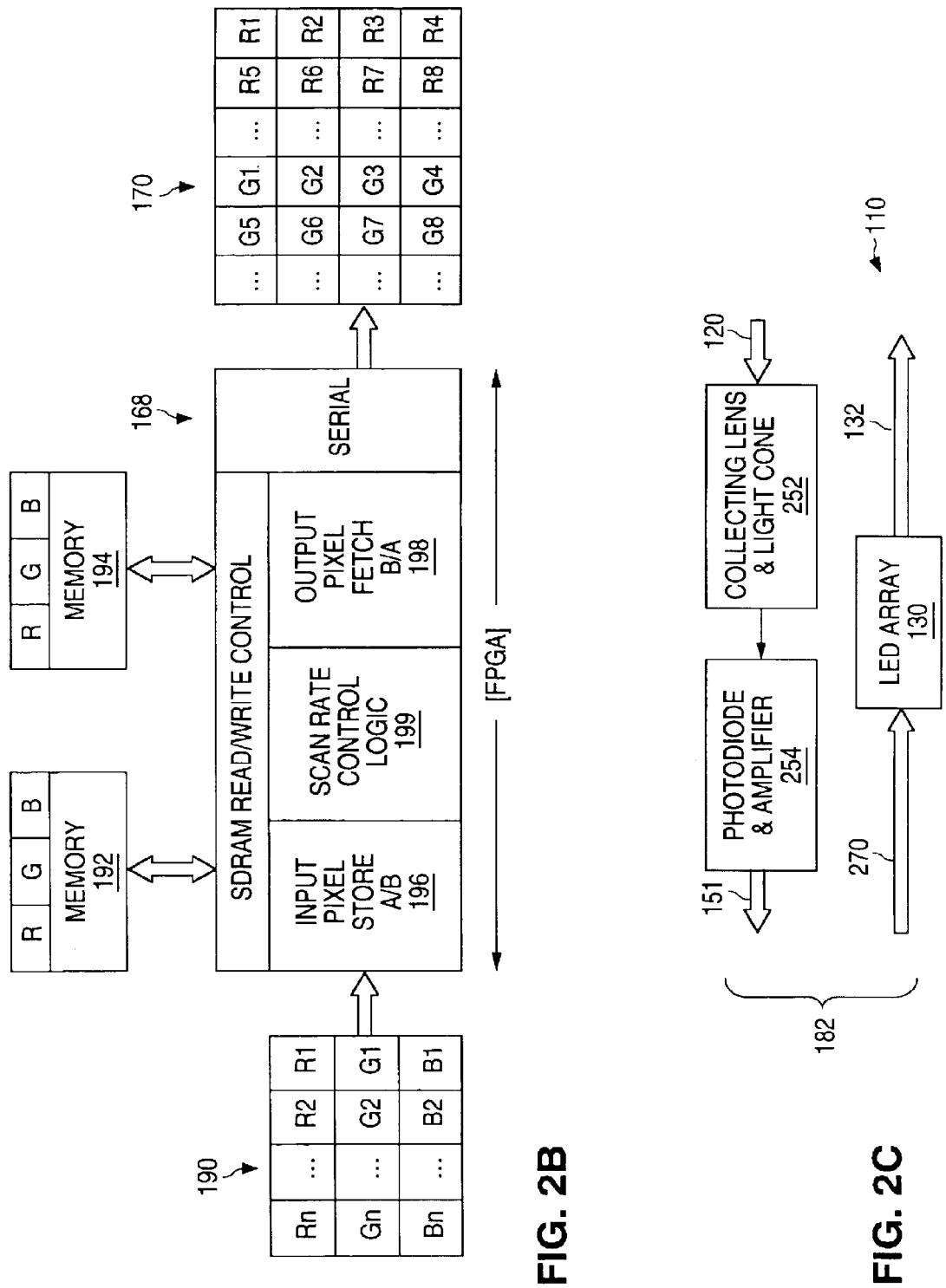

INFRARED AUDIO/VIDEO INTERFACE FOR HEAD-MOUNTED DISPLAY

CROSS REFERENCE TO RELATED APPLICATIONS

This application is related to application Ser. No. 09/305,092, filed May 3, 1999, now U.S. Pat. No. 6,101,038 issued on Aug. 8, 2000, the specification of which is expressly incorporated herein in its entirety.

This application is also related to Hebert, "Biocular Viewing System with Intermediate Image Planes for an Electronic Display Device", U.S. patent application Ser. No. 09/056,934, filed Apr. 6, 1998, commonly assigned, now U.S. Pat. No. 5,926,318 issued on Jul. 20, 1999, the specification of which is incorporated herein in its entirety.

FIELD OF THE INVENTION

This invention relates generally to image display systems and more particularly to infrared video and audio interfaces for head-mounted displays, principally eyeglass-mounted displays.

BACKGROUND

High quality medical remote imaging has gained increasing importance. This is particularly true of imaging during surgical procedures, most importantly minimally invasive procedures in which direct viewing of the surgical field is difficult. For example, a method for performing coronary artery bypass relies on viewing the cardiac region through a thoracoscope or other viewing scope (see for example Sterman et al. U.S. Pat. No. 5,452,733 and Gifford, III et al. U.S. Pat. No. 5,695,504). As a further example, a surgeon may perform a delicate vascular- or neuro-microsurgical reconstruction through a minimal incision under remote viewing. Remote imaging is now common in orthopedics, ophthalmology, urology, gynecology, anesthesiology, and other medical specifications.

In a conventional surgical environment, remote imaging is accomplished by attaching a video camera to an endoscope or other minimally invasive instrument and transmitting the video image via cable to a conventional CRT video monitor. This is often cumbersome in a crowded, brightly lighted operating room, where surgical team members are frequently moving around and the surgeon's view of the image screen is obstructed. Additionally, the CRT monitor is incapable of providing the surgeon with critical depth perception, since it is not stereographic.

Head-mounted displays (HMDs) potentially offer a method to overcome viewing obstructions typical in a surgical environment. While head-mounted displays have been designed, developed and deployed in military applications for many years, such displays are generally bulky, expensive, application-specific devices poorly suited to commercial or surgical applications. Additionally, users of head-mounted displays are frequently restricted in their range of motion by cumbersome interface cabling.

A compact HMD system requires a very small display device, such as those found in modern camcorder viewfinders, but with significantly higher resolution. A number of such devices are now becoming available, including transmissive and reflective liquid-crystal microdisplay devices and micro-mirror devices having resolutions at or in excess of VGA quality (640 pixels by 480 pixels) with pixel sizes on the order of 15 microns or less. However, they require integration into an ergonomic, well engineered and economical design. Most of these devices exhibit satisfactory image contrast only when illuminated and viewed at narrow angles of incidence, which compromises field of view, eye relief, and viewing comfort. Peripheral vision is also an important consideration.

A medical stereographic HMD system having dual display devices is described in Heacock et al. "Viewing Ocular Tissues with A Stereoscopic Endoscope Coupled to a Head Mounted Display (HMD)," http://www.hitl.washington.edu/publications/heacock/, Feb. 17, 1998. Kaiser Electro-Optics (2752 Loker Avenue West, Carlsbad, Calif. 92008 manufactures the "CardioView," "Series 8000," and "StereoSite" HMD display systems for Vista Medical Technologies. These systems are bulky, heavy, and expensive, and require two LCD display devices. For peripheral vision correction they require the user to wear the HMD over conventional corrective eyeglasses, aggravating user inconvenience and discomfort. Meyerhofer et al. U.S. Pat. No. 5,619,373, issued Apr. 8, 1997, describes a single display device involving beamsplitters for non-stereographic, biocular viewing.

The scan formats of video source devices, e.g., cameras and cassette players, are not directly compatible with typical solid state display devices. In particular, frame rates conforming with NTSC or PAL standards are too slow, and produce undesirable perceived flicker in solid state displays, which do not have the luminous persistence of phosphor screen displays, for example conventional TV displays. Therefore scan format and frame rate conversion are needed.

Heckman, U.S. Pat. No. 3,674,925, describes a wireless interface between a video camera source and a remote viewing display, employing a modulated optical video signal transmitter which doubles as a target illuminator. Hanson et al., U.S. Pat. No. 5,005,213, describes a wireless infrared/optical video interface directed to military applications. Puar et al., U.S. Pat. No. 5,650,955 describes an infrared interface for generating video images on a LCD or CRT display. However, the above cited U.S. Patents do not address, among other things, serial multiplexed color data, frame rate or scan format conversion.

Therefore, what is needed in the art is a compact, high resolution, high contrast microdisplay system, particularly for surgical viewing, that is suitable for head-mounted display use without requiring undue complexity or expense and that preferably supports biocular and/or truly stereographic viewing. The system should incorporate format and frame rate conversion to provide compatibility between solid state display devices and conventional video input sources. The system should provide good color fidelity and should incorporate ergonomic design for comfort and efficiency, including peripheral vision accommodation and minimal cabling.

SUMMARY

Apparatus according to the present invention includes a video or audio/video interface linking a base station with a remote video display. Video processing circuitry at the base station converts an input color video signal conforming to NTSC (525 lines) or PAL (625 lines) formats from a conventional source, e.g., a video camera, into a modulated video signal having a format appropriate to drive a solid state video display, e.g., a sequential color LCD display. The modulated video signal has a data structure containing a repetitive sequence of uniform frame times. Each frame time consists of substantially equal consecutive field times for each of three component color fields. Image information for each color field is encoded as a burst of pixel luminance data occupying roughly one-half of each field time. The data structure also typically contains embedded scan and frame control signals and an embedded pulse-amplitude audio channel. To minimize flicker with many such sequential color LCD displays, a frame rate of the order of 80 frames per second, or 240 color fields per second is required. This in turn requires a field time of roughly 4 msec. To handle this video data throughput typically requires a bandwidth of at least 100 MHz. A few such displays can operate at 60 frames per second without objectional flicker. These displays can then utilize roughly 5.3 msec. per field with at least 75 MHz. bandwidth.

To achieve the required frame rate, conversion is needed from conventional frame rates of 60 Hz or 50 Hz from input sources conforming to NTSC and PAL formats respectively.

The modulated video signal is transmitted to a remote receiver, located adjacent to a remote video display. The remote video display can be a mobile display, for example mounted in a headset worn by a user. A remote circuit interconnected between the receiver and the display demodulates the modulated video signal and controls the image data loading and color illumination of the display device. During each burst of data, the display device is loaded with pixel luminance data for a single color field. During the period between the end of one data burst and the onset of a subsequent burst, the display device is illuminated by a color LED corresponding to the color field just loaded. The process is repeated sequentially for the three color fields of the image frame, such that bursts of pixel luminance data alternate synchronously with illumination by an appropriate LED.

In some embodiments, two separate video display devices can be driven in parallel for a simplified binocular optical configuration.

In other embodiments, two separate video display devices (e.g., for stereographic viewing or alternate images on independently viewed displays) can be driven alternately. Each display is illuminated while the other display is loaded with video data. The two alternating burst datastreams are derived from a single time-multiplexed modulated video signal.

Although the video interface can transmit the modulated video signal through a conductive coaxial cable from the base station to the remote receiver, cables are cumbersome for mobile receivers, for example head-mounted displays, where they restrict the motion of a user. Alternatively, the video interface can transmit the modulated video signal on a modulated beam of infrared or other electromagnetic energy. Particularly, an infrared (IR) wavelength can be selected outside the visible region in the range of approximately 700 nm to approximately 1100 nm, where good conventional photodetectors, LEDs, and laser diodes are available. The IR beam can be guided through an optical fiber connecting the base station with the remote receiver, but this method has the same drawbacks as the coaxial cable.

Alternatively, the IR beam is generated by an array of IR LEDs and transmitted through a free atmospheric path. All the LEDs in the array emit an identical optical signal.

In one embodiment, the IR beam is projected onto a diffuse reflecting surface (for example the ceiling or an efficient scattering panel adjacent to the ceiling) by an array of conventional infrared LEDs with integral collimating lenses (typically for a ±10 degree radiation pattern from each LED) connected to the base station. The lensed LEDs typically create a 2 ft diameter on a scattering surface 6 feet away. The scattering surface is positioned and oriented such that the scattered IR signal is concentrated in a volume including the probable location of a remote receiver.

In one embodiment, the receiver includes a collecting lens assembly consisting of three coaxial components: a refractive lens with a conic sidewall and planar exit pupil, an inner cone with a diffusely reflective sidewall mating to the lens' conic sidewall, and an outer smooth reflective cone extended above the lens. The photodetector is optically cemented to the lens' planar exit pupil to couple some energy into the photodetector that would otherwise be lost to total internal reflection within the lens. This combination of elements dramatically enhances the photodetector's effective aperture over a wide angular field of view, thereby permitting the use of a smaller, wider bandwidth, less expensive photodetector to collect sufficient levels of infrared signal.

An optional prismatic dispersion plate overlying the outer conic cavity widens the collecting angle of the assembly. An optional optical bandpass filter is positioned over the assembly.

In some embodiments, one or more optical elements of the collecting lens assembly are aspheric. Transmissive optical elements are typically made from transparent polymeric material, for example polymethyl methacrylate, polycarbonate, and ULTEM® grade polycarbonate manufactured by General Electric Company.

In some embodiments, the interface includes a return audio link that provides return audio communication from the receiver location to the base station. The return audio can modulate a LED, which emits an audio modulated IR signal through the atmosphere. The audio modulated IR signal is then detected by a separate receiver connected to the base station, where the audio data is processed and restored. In one embodiment, the audio receiver has the same three-component coaxial structure as the remote receiver.

The present invention is better understood upon consideration of the detailed description below, in conjunction with the accompanying drawings.

BRIEF DESCRIPTION OF THE DRAWINGS

The present invention may be better understood, and its numerous objects, features, and advantages made apparent to those skilled in the art by referencing the accompanying drawings. For simplicity and ease of understanding, common numbering of elements within the illustrations is employed where an element is the same in different drawings.

FIG. 2B is a functional block diagram illustrating the operation of a scan rate converter;

FIG. 2C is a block diagram of a transceiver module;

DETAILED DESCRIPTION OF THE EMBODIMENTS

The following is a detailed description of illustrative embodiments of the present invention. As these embodiments of the present invention are described with reference to the aforementioned drawings, various modifications or adaptations of the methods and or specific structures described may become apparent. These descriptions and drawings are not to be considered in a limiting sense as it is understood that the present invention is in no way limited to the embodiments illustrated.

Figure 1A:
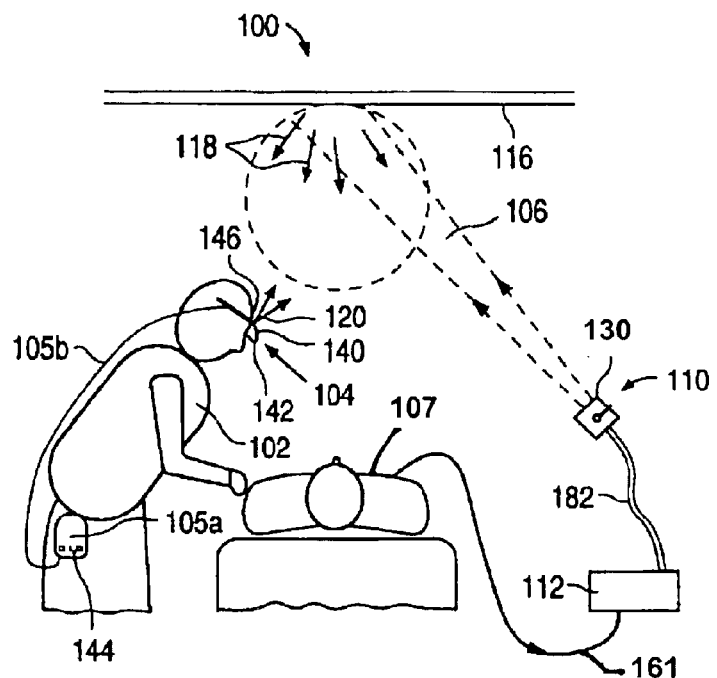
FIG. 1A is a schematic view of a surgical environment including an infrared video interface for a head-mounted display, in accordance with the present invention.

FIG. 1A is a schematic view of a surgical environment including an infrared video interface 100 for a head-mounted display, in accordance with the present invention. A user 102, e.g., a surgeon or assistant over a surgical patient 107, wears a headset 104, containing a remote video display device 140 and a remote electronic circuit 142, including ancillary optical, audio, and electronic apparatus, described in more detail below. In some embodiments, all of the receiving, processing, audio, and display functions relating to the head-mounted display are performed within headset 104. Alternatively, some of these functions are performed within an optional utility module 105a attached, for example, to the clothing or belt of user 102, and connected to headset 104 by a utility cable 105b. Batteries 144 configured to power the respective head-mounted display functions can be mounted at headset 104 or optionally at utility module 105a. A remote mobile video bandwidth receiver 146 located, e.g., at headset 104, receives a diffusely reflected infrared signal 118 carrying video and/or audio data on a modulated beam of electromagnetic energy. A modulated infrared signal 106 is transmitted through the atmosphere from an array 130 of conventional IR LEDs with integral collimating lenses (typically for a +10 degree radiation pattern from each LED) within transceiver module 110, which is connected to a base station 112 by a bundle of cables 182. The lensed LEDs typically create a 2 ft diameter circle on a diffusely reflective scattering surface 6 feet away. Alternatively, transceiver module 110 is integral with base station 112. An imaging system (not shown), e.g., an endoscopy video camera, within surgical patient 107 provides a video image via an appropriate communication line 161 to base station 112.

The LED array 130 is significantly less expensive than a single laser diode of equivalent power and offers a significant reliability advantage over the laser diode. In addition, the spatially distributed nature of the LED array 130 avoids the high power density of the laser diode and minimizes the possibility of total blockage of the signal path to the headset. The lower power density of the LED array 130 avoids the design considerations and concerns related to potential eye damage and associated regulatory controls, such as FDA regulations.

In the embodiment of FIG. 1A, lensed LED array 130 projects modulated IR signal 106 through the atmosphere onto a diffusely reflective target area of the ceiling 116 or a surface (not shown) mounted adjacent ceiling 116. Infrared signal 106 is scattered through the atmosphere from the diffuse target area as diffusely reflected IR signal 118, a portion of which illuminates headset 104. In some embodiments, the diffuse target area (e.g., ceiling 116), provides a substantially cosine (Lambertian) pattern of diffusely reflected IR signal 118. Alternatively, the diffuse target area has a lenticular or other well known surface structure, providing a directionally preferred scattering pattern of scattered infrared signal 118.

In some embodiments, headset 104 provides a return audio signal back to base station 112. A return IR fan 120 carries the modulated audio signal at least in part through an atmospheric transmission path, generally retracing the transmission paths of diffusely reflected IR signal 118 and projected infrared signal 106.

Although a surgical environment is depicted in FIG. 1A, in other embodiments similar configurations including an infrared video interface 100 for a head-mounted display, in accordance with the present invention, are applied to a variety of environments.

Figure 1B:
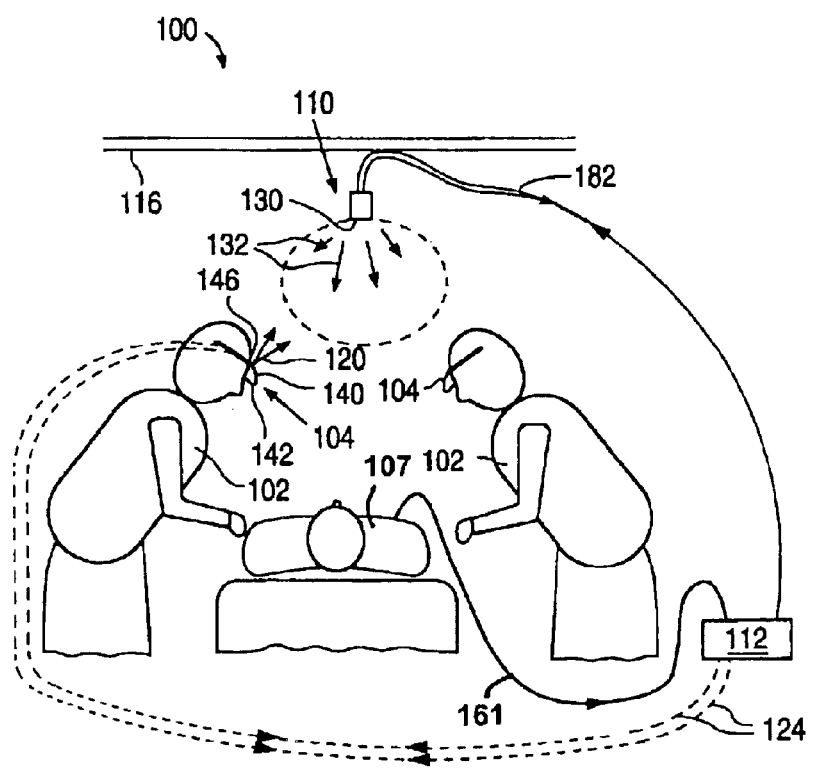
FIG. 1B is a schematic view of an alternative surgical environment to that of FIG. 1A.

FIG. 1B is a schematic view of an alternative surgical environment to that of FIG. 1A. Transceiver module 110 is attached above the working space of users 102, e.g., suspended from ceiling 116 or other elevated support, and is connected with base station 112 by coaxial cable 182. An array 130 of IR LEDs, described in more detail below, is mounted in transceiver module 110 and is configured to direct an IR beam 132 within the volume including the probable location of respective users 102.

Many of the properties of infrared video interface 100, in accordance with the present invention, derive from the requirements of head-mounted video display 140. For some embodiments, these requirements are described in Hebert, U.S. patent application Ser. No. 09/056,934, cited above. In some embodiments, headset 104 does not require a frame memory.

To simulate full color using a monochromatic display, as described in Hebert, cited above, the display device is sequentially illuminated with red, green, and blue light sources, for example LEDs. When this sequential illumination occurs at a high enough frequency, a user's eye merges the sequence of colors and creates a perception of full color. In accordance with the present invention, infrared video interface 100 carries each sequential field of red, green, or blue video information as a burst of data. The sequence is repeated at a data rate, such that full motion and full color images are simulated.

A solid state display is preferably illuminated at approximately an 80 Hz frame rate (a 240 Hz field rate representing a three-color sequence for each frame) to minimize the amount of flicker perceived by the eye. This is equivalent to one color field each 4.16 msec. However, the NTSC (National Television Standards Committee) video format provides a 60 Hz frame rate, whereas PAL (phase Alternating Line) video format provides a 50 Hz frame rate. Both of these frame rates are too slow to prevent perceived flicker in the solid state display. Because of luminous persistence of phosphors, conventional video displays, e.g. TV screens, are more tolerant of the slower frame rates. Therefore, frame rate conversion is performed in base station 112. In accordance with embodiments of the present invention, the method adopted to increase the effective frame rate is cyclical repetition of one or two of the sequential red, green, or blue fields. The specific scheme applied depends on whether the input source conforms with an NTSC or PAL format. For further discussion of conventional video standards and sources, see for example K. Jack, "Video Demystified, A Handbook for the Digital Engineer," Second Edition, 1996, published by HighText Interactive, Inc., San Diego.

From an NTSC source, interlaced color frames are received at a rate of 60 Hz, (or 16.66 msec per frame). If RGB indicates a new input three-color field sequence (red, green, blue), and if rgb indicates repeated color fields (red, green, blue) stored in the memory of base station 112, then the following sequence can be generated: RGBrGBRgBRGb RGBrGBRgBRGb. The insertion of one repeated output color field for each consecutive set of three input color fields increases the perceived frame rate and thereby reduces perceived flicker. The repeated color selection and the consecutive input color field set are rotated cyclically, thereby preserving the original color sequence and retaining color fidelity. By converting to four separate color fields every 16.66 msec, then each individual color field is sent every 16.66/4=4.16 msec, resulting in 240 individual color fields transmitted per second. The effective three-color frame output rate is 240/3=80 "full color" frames per second.

From a PAL source, interlaced color frames are received at a rate of 50 Hz (or 20.0 msec per frame). If RGB indicates a new input three-color field sequence (red, green, blue), and rgb indicates repeated color fields (red, green, blue) stored in the memory of base station 112, then the following sequence can be generated: RGBrgBRGbrGBRgb RGBrgBRGbrGBRgb.

The insertion of two repeated output color fields for each consecutive set of three input color fields increases the perceived frame rate and thereby reduces perceived flicker. The repeated color selections and the consecutive input color field set are rotated cyclically, thereby preserving the original color sequence and retaining color fidelity. By converting to five separate color fields every 20 msec, then each individual color field is sent every 20.0/5=4.0 msec, resulting in 250 individual color fields transmitted per second. The effective three-color frame output rate is 250/3=83.3 "full color" frames per second.

The total available field time (either 4.16 msec for NTSC or 4.0 msec for PAL) is partitioned into several phases, including: (1) erase display, (2) load display, and (3) illuminate display with an appropriate red, green, or blue LED. In the present embodiment, the display loading time is selected to be approximately 2 msec for each color field of information. During this 2 msec interval, each of the 800× 600 pixels in the display is loaded with luminance data, namely, some gradation between black and white. Thus, all 480,000 of the pixels must be loaded in 2 msec or less. This corresponds to a throughput of 480,000 pixels/2 msec=240 million pixels per second. Thus, during 2 msec of each color field time, infrared video interface 100 transmits the equivalent of 240 million pixels per second, roughly a pixel every 4 nsec.

These times may require adjustments for particular microdisplays, since some are more prone to flicker than others. For example, reflective sequential-color microdisplays manufactured by The MicroDisplay Corporation, 3055 Research Drive, San Pablo, Calif., work without objectionable flicker at the native frame rates of NTSC and PAL (60 frames/sec and 50 frames/sec, respectively). This eliminates the requirement for the infill color fields, allowing a simplification of the electronics for a simple RGBRGB sequence. It correspondingly reduces field times (roughly 5.6 msec. for NTSC; 6.7 msec. for PAL) and consequent bandwidth requirements.

Since the signal is encoded using a baseband (no carrier frequency) amplitude modulation (AM) protocol, the IR interface data transport scheme can be described as "burst mode amplitude modulation". Amplitude modulation is preferred to simplify the receiver design. The encoding scheme can alternatively utilize pulse modulation without changing the fundamental structure of IR video interface 100. However, receiver circuits would need to convert the pulse modulation back into amplitude modulation to be compatible with a display of the present embodiment.

Figure 1C:
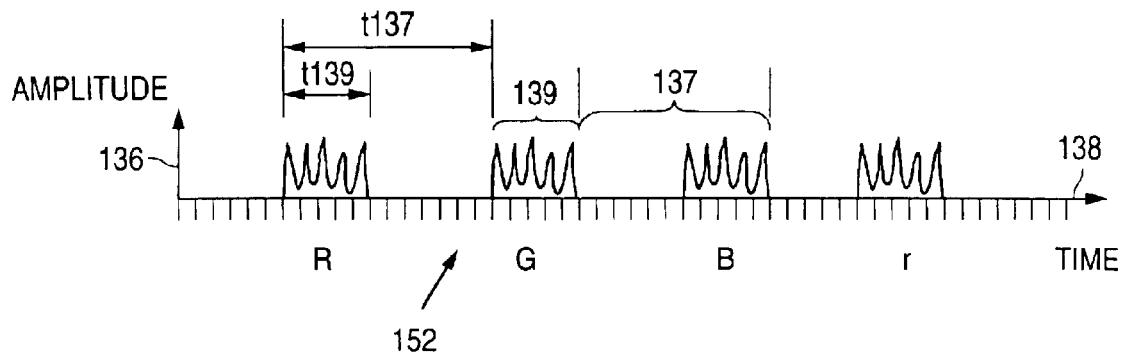
FIG. 1C is a graphic representation of a typical burst mode data structure for a solid state video display, in accordance with an embodiment of the present invention.

FIG. 1C is a graphic representation of a typical burst mode data structure for a solid state video display, in accordance with an embodiment of the present invention. In FIG. 1C, signal amplitude 136 is shown as a function of time 138. Sequential input color fields are labeled R, G, and B, followed by a repeated color field stored in the memory of base station 112 labeled r. A repetitive sequence of horizontal sync pulses 152 provides basic synchronization for the burst mode structure. An individual color field 137 has a time duration t137, or approximately 4 msec. The pixel luminance data 139 within each color field is transmitted as a data burst and has a time duration t139, or approximately 2 msec.

Figure 1D:
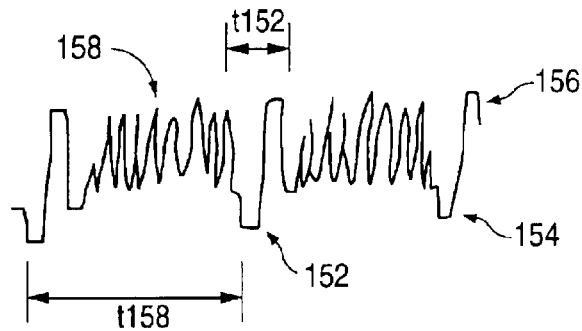
FIG. 1D is graphic representation of a typical horizontal line within the data burst structure of FIG. lC, illustrated on an expanded time scale.

FIG. 1D is graphic representation of a typical horizontal line within data burst 139 of FIG. 1C, illustrated on an expanded time scale. Within each color field burst R, G, B, r of FIG. 1C is a series of horizontal sync pulses 152. A typical horizontal sync pulse 152 has a substantially rectangular waveform with an amplitude that defines a grey scale between black 154 and white 156. Between consecutive horizontal sync pulses 152 is one horizontal line of analog pixel data 158, e.g. 800 pixels to a horizontal line. The full width t152 of a horizontal sync pulse 152 provides a clock basis for data burst timing and has a duration typically equal to that of 32 pixels, which corresponds to approximately 125 nsec. The time duration t158 between consecutive horizontal sync pulses is approximately 3.25 μsec in the example shown.

The design of IR video interface 100 is adaptable for driving one or two video/audio channels. In the single channel mode, half of each color field time is used for data transfer, and the other half is used for illumination. In the dual channel mode, one half of each color field time is used for data transfer to a first channel, and the other half of the time is used for data transfer to the second channel. First and second channels' displays are alternately illuminated, such that the illumination occurs for one display while data is transferred to the other display, as described below in more detail. Two data channels can be used for presentation of true stereo imagery or, alternatively, a different view (i.e., inverted view or different video source) sent to different observers.

If IR video interface 100 is required to transmit data for two display channels, then each channel can be alternately loaded and illuminated. Thus the interface carries burst mode image data for a first channel during 2 msec, while a second channel is illuminated. Likewise, during the next approximately 2 msec interval, the first channel is illuminated while the interface transmits image data to the second channel. This scheme can be described as time division multiplexing (or time-duplexing) with burst mode modulation.

In an imaging system, bandwidth manifests itself as the ability to resolve fine spatial details, such as the sharp edges of objects. More specifically, the measured bandwidth of a high quality endoscopy video camera is approximately 5.33 MHz for each individual RGB channel. An example of such a video camera is the Telecam SL NTSC, sold by Karl Storz Endoscopy, 91 Carpenter Hill Road, Charlton, Mass. 01507. The Storz camera bandwidth represents approximately 275 horizontal cycles (black-white transitions). This is based on a 60 Hz (525 line) system using a standard 52 $\mu$sec horizontal line time, i.e. (5.33 MHz/52 $\mu$sec) approximately 275 cycles per line. The IR video bandwidth required to deliver 275 cycles in one display line time, namely t158 seconds as shown in FIG. 1D, is about 85 MHz, i.e. (275 cycles/3.25 $\mu$sec). Bandwidth calculations for more cycles (higher resolutions) yield about 100 MHz for VGA (320 horizontal cycles) or 125 MHz for SVGA (400 horizontal cycles). In light of these considerations, the infrared interface must support a bandwidth of about 85 MHz to display high quality images from traditional NTSC or PAL sources, and greater than 100 MHz for VGA or SVGA computer generated images.

Conventional bandwidths for audio communication channels are only of the order of 20 KHz. Therefore, an audio channel can easily be added or embedded as a subcarrier in a video channel having bandwidth of the order of 100 MHz. In the discussion below, a video interface, channel, or signal is generally assumed to include dual audio/video capability.

Transmitting sequential color fields across IR video interface 100 increases the bandwidth requirement, but reduces the complexity of receiver and color decoder circuits, described below in more detail. Additionally, repeating selected color fields in the sequence enables an increase in the rate of updating a display frame, thereby reducing perceived flicker.

In addition to bandwidth (image resolution), signals transmitted over an interface must have a high signal to noise ratio (S/N) to provide acceptable image quality. S/N ratios are conventionally measured in decibels (dB), which are logarithmic units. For example, a 40 dB S/N ratio represents one part of noise in 100 parts of signal, i.e., one per cent noise. This S/N ratio equates to the EIA standard for "fine quality" broadcast television, which is seen under nearly ideal reception conditions. For a detailed discussion, see for example Table 16 and related text of "Satellite Technology, An Introduction," by Andrew F. Inglis, 1991, published by Focal Press. In accordance with the present invention, IR video interface 100 is designed to meet a higher S/N standard than 40 dB.

The high bandwidth and signal to noise requirements discussed above require that the IR composite video and audio transmitter and return audio receiver (e.g., transceiver module 110) be located in a position where the IR energy is efficiently directed toward the area of the receiver, namely headset 104. FIG. 1B illustrates transceiver module 110 positioned above users 102 and connected to base station 112 by coaxial cable 182. As shown in FIG. 1B, the IR signal 132 from transceiver module 110 is generated by an LED array 130, described below in more detail. In FIG. 1A, transceiver module 110 is located closer to base station 112, and infrared signal 106 is partially collimated by lensed LED array 108 and aimed at a diffuse surface above users 102. This configuration is less efficient than that of FIG. 1B, since IR signal 106 undergoes an extra diffuse reflection.

Figure 2A:
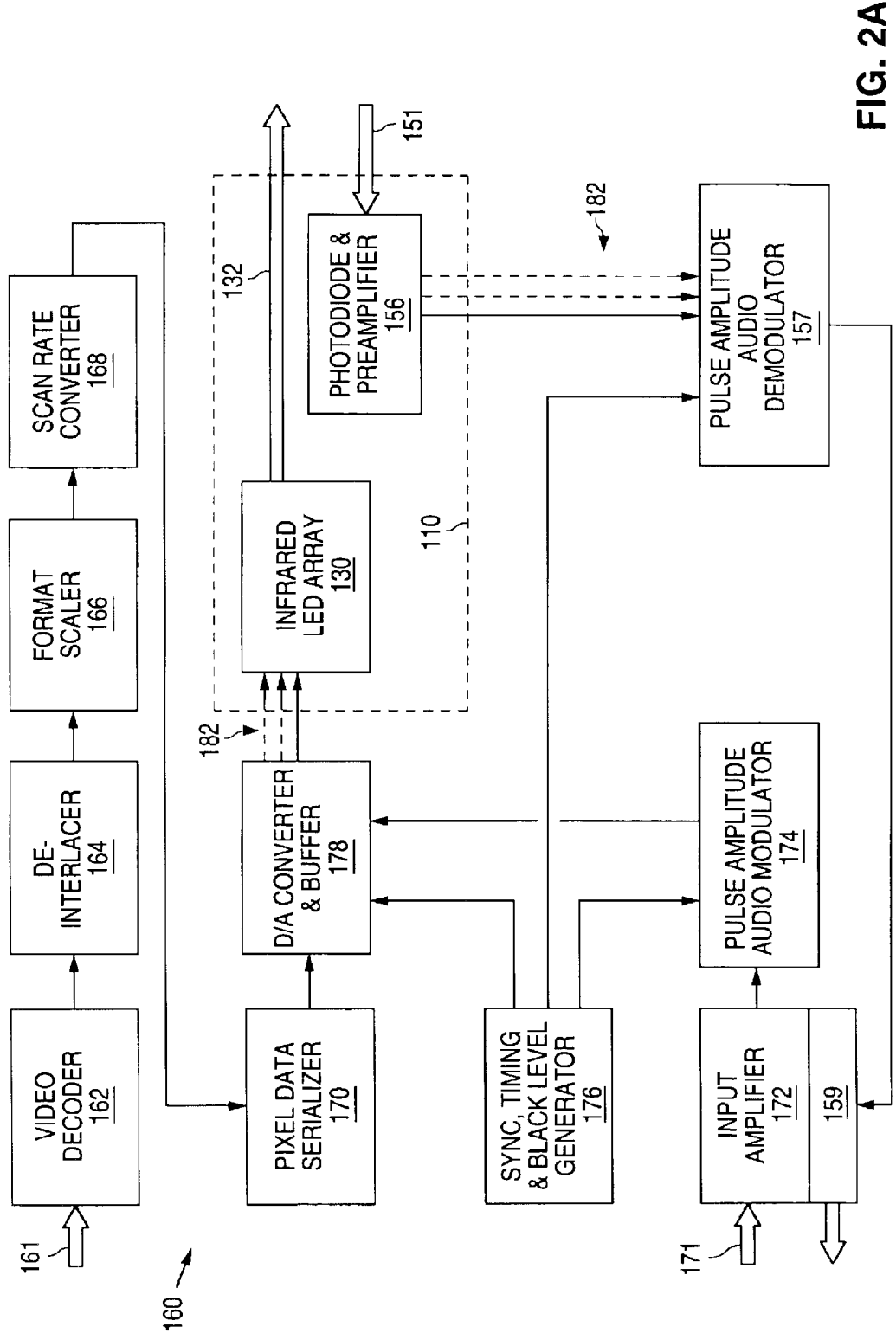
FIG. 2A is a functional block diagram of a video processing circuit located, for example, in a base station.

FIG. 2A is a functional block diagram of a video processing circuit 160 located, for example, in base station 112. An input video signal 161 enters at the upper left hand corner and is applied to a video decoder 162. Input signal sources (not shown) include conventional video sources, such as NTSC, PAL, or SECAM encoded composite sources, e.g., cameras, and 525/625 line component sources such as YUV or S-Video. Video decoder 162 consists substantially of a conventional Digital Multistandard Color Decoder IC, for example Philips Semiconductors, 811 East Arques Avenue, Sunnyvale, Calif. 94088, Model SAA 7110 Decoder.

In video decoder 162 the NTSC/PAL/SECAM analog video signals are demodulated and converted to digital format luminance and chroma (color) for processing by subsequent circuit modules. Video decoder 162 also provides scaling and offset of various video components such as hue, brightness, and saturation for user preferences.

Digitally formatted luminance and chroma signals from video decoder 162 are applied to a de-interlacer 164, which converts the signals into digital RGB format and then combines the odd and even line fields into a sequential frame format. De-interlacer 164 consists substantially of a conventional interlaced to sequential frame converter, for example, Genesis Microchip, Inc., 2071 Landings Drive, Mountain View, Calif. 94043, Model gmVLD8 De-Interlacer, with an external pixel buffer RAM memory. Since the odd and even scan fields are separated in time by either 1/50 or 1/60 sec., de-interlacer 164 interpolates between the two fields to minimize tearing of vertical lines when the image is rapidly panned.

The resulting RBG color pixel data are applied to a format scalar 166, which interpolates to a higher pixel resolution as required for the display. For example, VGA format data (640×480 pixels) is scaled to SVGA format data (800×600 pixels). Format scaler 166 consists substantially of a conventional image scaling and anti-aliasing IC, for example, Genesis Microchip, Inc., 2071 Landings Drive, Mountain View, Calif. 94043, Model gmZ1 Scaler. Scaling algorithms familiar in the art are used to minimize video artifacts created during the scaling process.

After scaling, the RGB pixel data are applied to a scan rate converter 168, which converts the video input frame rates of 50/60 Hz to 83.3/80 Hz to minimize the potential for visible flicker in the display. Scan rate converter 168 then outputs the frame data in separate red, green, and blue fields. Scan rate converter 168 is implemented using a Field Programmable Gate Array (FPGA), for example Xilinx, Inc., 2100

Logic Drive, San Jose, Calif., Model 4010 PQ160 FPGA, and a synchronous high speed SDRAM.

FIG. 2B is a functional block diagram illustrating the operation of scan rate converter 168. The digital RGB color pixel data 190 from format scaler 166 enters scan rate converter 168 from the left and is stored in one of two memory banks 192, 194. Each memory bank 192, 194 is segmented into red, green, and blue field storage labeled R, G, and B, to facilitate field sequential color imaging. Each memory segment can hold the red, green, or blue color value, for example an 8-bit quantity, for each of the 480,000 pixels in an SVGA (800×600) field. An input pixel store function 196 stores video frames alternately in memory bank 192 or 194.

Whereas input pixel store function 196 writes data into memory banks 192 and 194, an output pixel fetch function 198 reads data from the respective memory bank 192, 194, that was previously filled with data. In other words, input pixel store and output pixel fetch functions 196 and 198 respectively never overlap their use of the same memory bank 192 or 194. Rather, they alternate memory banks, thereby de-coupling input data from output data.

A scan rate control logic function 199 accepts data at a 50/60 Hz rate supplied by a video source and outputs the data at a higher rate, namely, 83.3/80 Hz. Scan rate control logic function 199 controls the flow of data in the sequential red, green, and blue fields, instructing output pixel fetch function 198 to insert repeating color fields to convert the effective frame rate. In some embodiments, headset display 140 requires four pixels of data to be loaded during each input cycle. In these embodiments, output pixel fetch function 198 is instructed to read four pixels, e.g., 32 bits, simultaneously and to present these pixel data in a burst format to a pixel data serializer 170.

Red, green, and blue color field data are serialized in pixel data serializer 170 (see FIG. 2A) into a stream suitable for transmission over a wireless link. In addition to serialization, pixel data serializer 170 inserts video synchronization information to define horizontal, vertical, and color syncs. Pixel data serializer 170 converts the parallel digital pixel color data into amplitude modulated signals using conventional digital to analog converters (DAC's). It then outputs the analog signals, e.g., four pixel values, into a high speed serial data stream suitable for transmission over the wireless (serial) link. Conventional sample-and-hold amplifiers are used to delay the analog signals for conversion to a serial analog data stream, as described above in connection with FIG. 1C.

Referring to FIG. 2A, optionally, an input audio signal 171 from a microphone or other conventional source (not shown) enters an input amplifier IC 172 with level control and high frequency boost to improve overall S/N ratio. The audio signal is then applied to a pulse amplitude audio modulator 174 which converts the amplitude modulated signal to an amplitude pulse. This pulse is inserted just prior to the beginning of video data within each horizontal scan as determined by sync, timing and black level generator 176, which controls all system timing. The generator's 176 timing functions are mirrored in exact synchronization by generator 334 of FIG. 3D in the remote receiver, i.e., headset, for extraction and reconstruction of data. All timing and reference level data is combined with the analog-converted digital pixel data in D/A Converter & Buffer 178, which consists of a high-speed video quality D/A (digital/analog) converter, summing amplifier, and video line driver. When combined with the pixel data, the audio signal is recovered from the video via sampling using reconstructed timing information within the remote receiver. The audio pulse amplitude is then conventionally converted to a normal analog audio signal, e.g., for headphones, using a sample-and hold circuit in detector 324 of FIG. 3D.

The combined serial video data and optional modulated audio data from D/A Converter and Buffer 178 is transmitted through a bundle of coaxial cables to infrared LED array 130. IR LED array 130 is selected for its high frequency modulation capability, which transmits the signal as an amplitude modulated IR beam. In some of such embodiments, infrared LED array 130 comprises one or more high-frequency infrared LED's, for example, Infineon, Inc., 10950 North Tantau Avenue, Cupertino, Calif. 95014 Model SFH4200 series of wide-angle SMT devices, or model SFH4500 series of lensed $T^1$ ¾ devices.

Optionally, a return audio signal 151 from headset 104 (transmitted through the reverse-path free space infrared link) is received by photodiode and preamplifier 156, which converts the modulated optical signal to a low level modulated electrical signal, amplifies the low level signal, buffers it for transmission over coaxial cable 182, and applies it to pulse amplitude audio demodulator 157, which recovers the audio signal using sample-and-hold technology driven by timing generator 176. The audio signal is frequency conditioned to improve the signal to noise ratio at high frequency and to restore the overall audio fidelity of the signal. Finally, the audio signal is processed by a line driver IC amplifier with level control circuits 159 for output coupling to conventional audio output equipment (not shown).

In another embodiment, the return audio signal is digitized with a simple A/D converter within headset 104. It is then formatted, stored and restructured digitally by a PIC controller within timing generator 334 of FIG. 3D as a series of full-amplitude pulses occupying a time slot normally used for a full horizontal line of video; for example, every eighth line. The video normally occupying these lines is then blanked and delayed for IR transmission until the following lines, thereby adding 600/8 or 75 lines to the SVGA format. As with other timing functions, the video blanking and audio pulse formatting is controlled in base station 160 of FIG. 2A by generator 176 and synchronously controlled by headset timing generator 334 in FIG. 3D. Audio information is transmitted as an IR series of pulses in the same way by headset LEDs 306 in FIG. 3A, received by collecting lens and lightcone 252 in tranceiver module 110, and sent through coaxial cable 151 in cable bundle 182 to base station 112,where it is digitally decoded and converted to analog audio for equivalent use. While this digital embodiment has the disadvantage of increasing the video bandwidth by 675 lines/600 lines, or 12.5%, it has the advantage of decreasing headset LEDs 306 power requirements for equivalent S/N ratio to the pulse amplitude format; thereby extending the operational life of headset batteries 104.

In FIGS. 1A and 1B, transceiver module 110 is used to distribute (broadcast) combined audio and video signals from base station 112 to headset 104. Transceiver module 110 also serves as a collection and relay module for optional IR audio signal 120 returning from headset 104. In the embodiment shown in FIG. 1A, transceiver module 110 is located below the area where headset 104 is used. Alternatively, in the embodiment shown in FIG. 1B, transceiver module 110 is located above and proximate to the area where headset 104 is used. This placement optimizes the signal distribution and provides the best image quality by minimizing reflections along the IR signal path. Transceiver module 110 can be implemented with a bundle of cables 182 from base station 112.

FIG. 2C is a block diagram of tranceiver module 110. The combined video and optional audio infrared signals from base station 112 are carried by coaxial cable 270 through bundle of cables 182 to an IR LED array 130. The IR LED array 130 transmits IR signal pattern 132 toward remote receiver 146, e.g., headset 104.

Optionally, a return modulated audio IR signal 120 from headset 104 is collected by a collecting lens and light cone 252 in transceiver module 110, and the collected light directed to a photodiode and amplifier 254. Photodiode and amplifier 254 convert and amplify the optical signal to produce an electric audio signal, which drives coaxial cable 151 through bundle of cables 182 to base station 112.

Figure 2D:
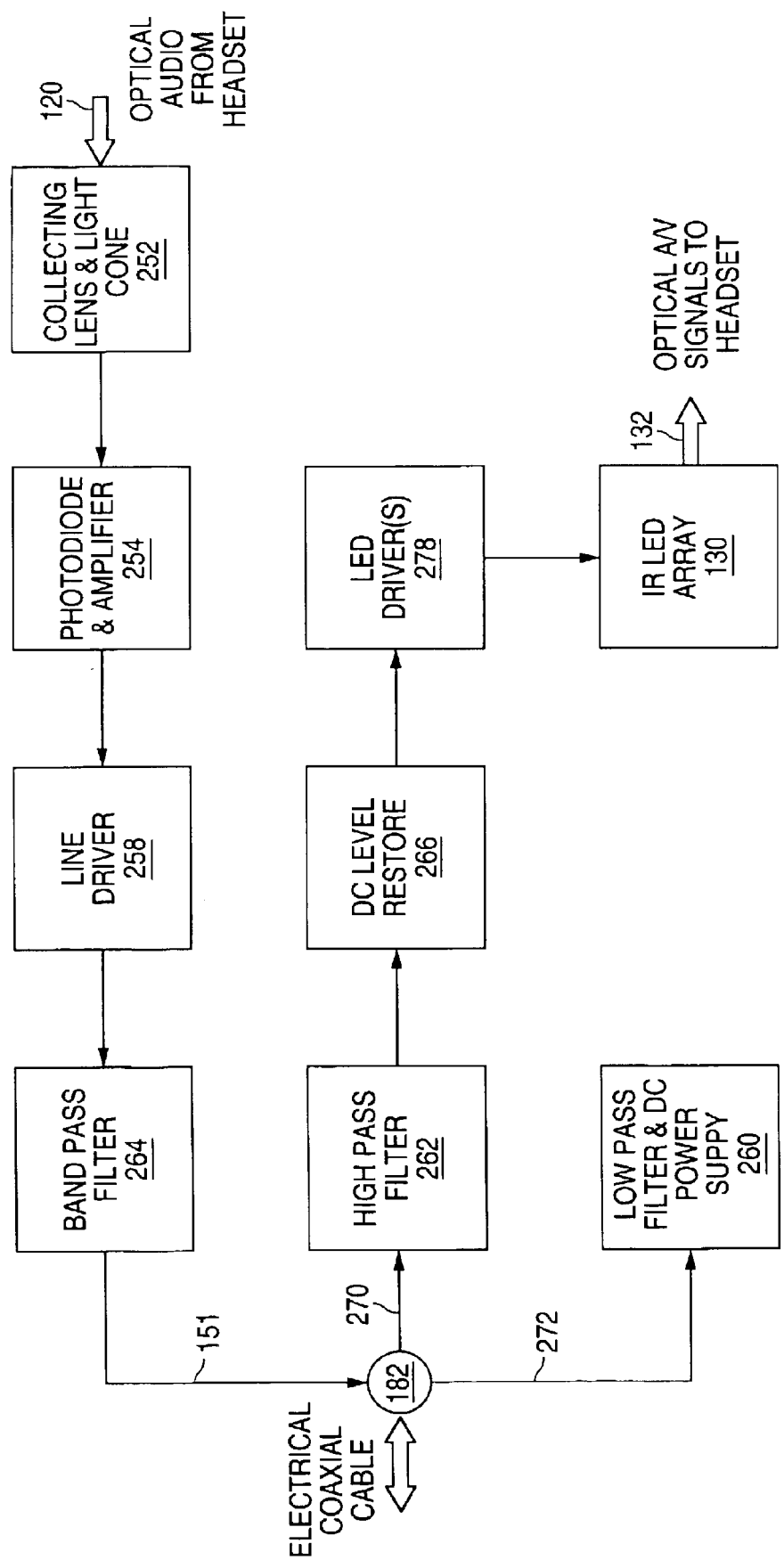
FIGS. 2D and 2E are more detailed transceiver schematic block diagram, in accordance with further embodiments of the present invention.

FIG. 2D is a more detailed transceiver schematic block diagram, in accordance with a further embodiment of the present invention. Transceiver circuit 110 is connected with base station 112 through electrically conducting coaxial cable 182, which carries respective video signals 270, audio signals 151, and DC electrical power 272. DC power 272 from coaxial cable 182 is filtered from audio and video signals by a low pass filter and power supply 260, which provides power for the active elements of transceiver circuit 110. Video signal 270 from coaxial cable 182 is filtered through a high pass filter 262 and is applied through a DC level restore module 266 to LED drivers 278, which drive an IR LED array 130. The IR LED array produces IR beam 132.

Optional return audio signal on return IR beam 120 is transmitted through collecting lens and lightcone 252 onto photodiode and amplifier 254 where it is converted into an electrical signal. The audio electrical signal from photodiode and amplifier 254 is amplified by a line driver 258 and is then filtered through a bandpass filter 264 prior to transmission as audio carrier signal 151 through coaxial cable 182 to base station 112.

Figure 2E:
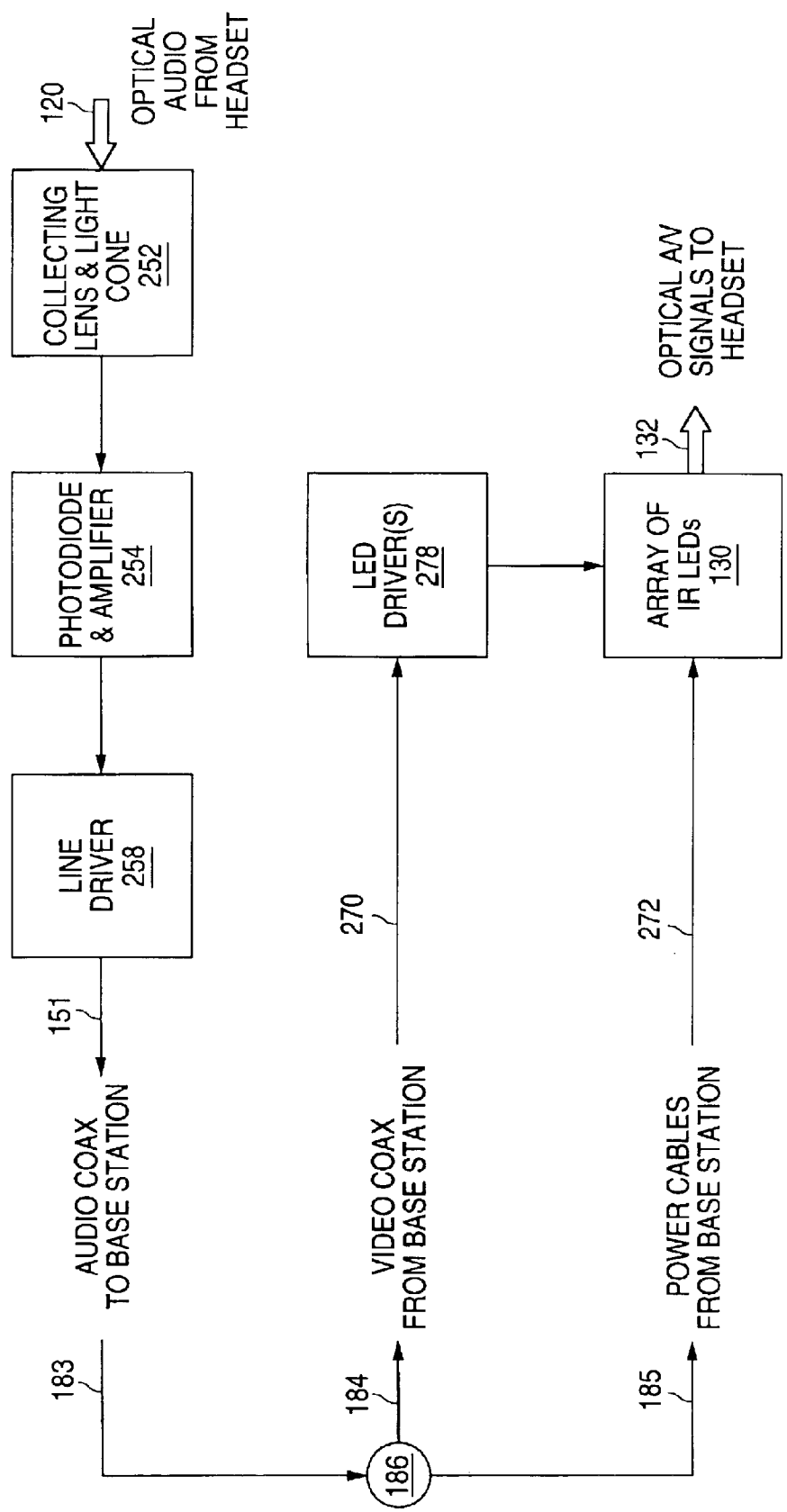

FIG. 2E is a more detailed transceiver schematic block diagram, in accordance with a further embodiment of the present invention. Transceiver circuit 110 is connected with base station 112 through a bundle of cables 182, which comprises a video coaxial cable 184 carrying video signals 270, an audio coaxial cable 183 carrying audio signals 151, and power cables 185 carrying DC electrical power 272. Video signal 270 from video coaxial cable 184 is applied to LED drivers 278, which drives an IR LED array 130. The IR LED array produces an IR beam 132.

Optional return audio signal on return IR beam 120 is transmitted through collecting lens and lightcone 252 onto photodiode and amplifier 254 where it is converted into an electrical signal. The audio electrical signal from photodiode and amplifier 254 is amplified by a line driver 258 and is transmitted as audio carrier signal 151 through audio coaxial cable 183 to base station 112.

Figure 3A:
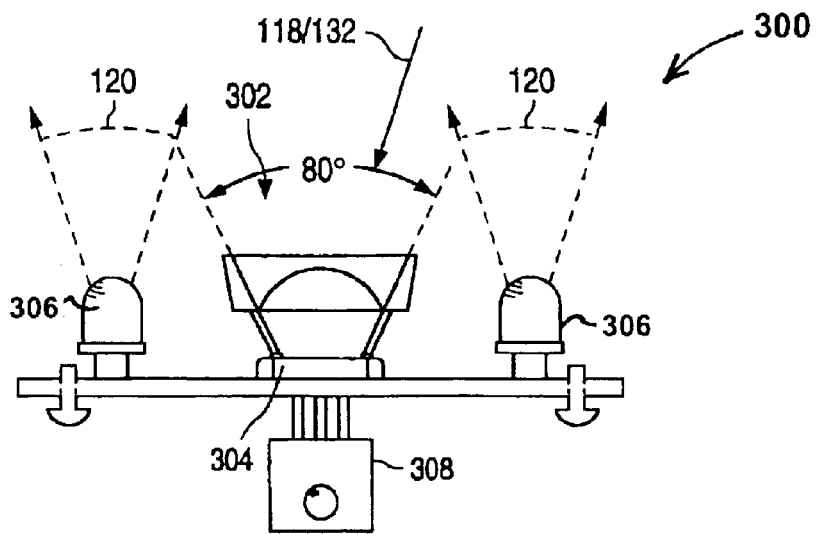
FIG. 3A is a schematic front view of an IR module incorporated in a headset, containing components of the IR video interface.
Figure 3B:
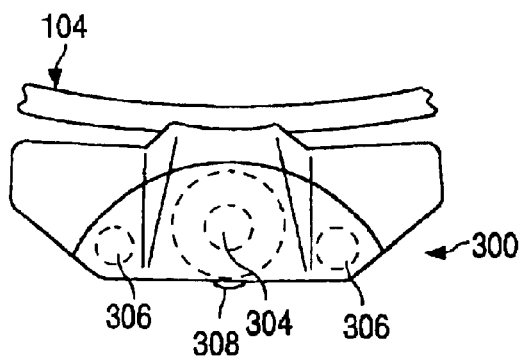
FIG. 3B is a top schematic view of an embodiment of a headset including an IR module.
Figure 3C:
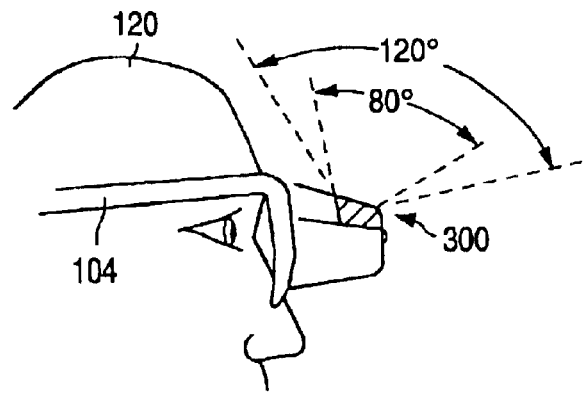
FIG. 3C is a side schematic view of a user wearing an embodiment of a headset including an IR module.

The optical components mounted at headset 104 are complementary to those mounted at transceiver module 110. FIG. 3A is a schematic front view of an IR module 300 containing components of IR video interface 100 incorporated in headset 104. FIGS. 3B and 3C are top and side schematic views, respectively, of a user wearing an embodiment of headset 104 including IR module 300. In FIGS. 3B, 3C, and 1A, the example headset 104 is a surgical eyewear frame including a pair of eyeglasses, and IR module 300 is coupled to a front portion of the frame above the eyeglasses. IR module 300 is mounted away from the user's peripheral vision field and above the LCD and associated display optics (see Hebert, cited above), thereby providing a substantially unobstructed wide angle reception path to the ceiling or to an overhead transmitting LED array.

Figure 3D:
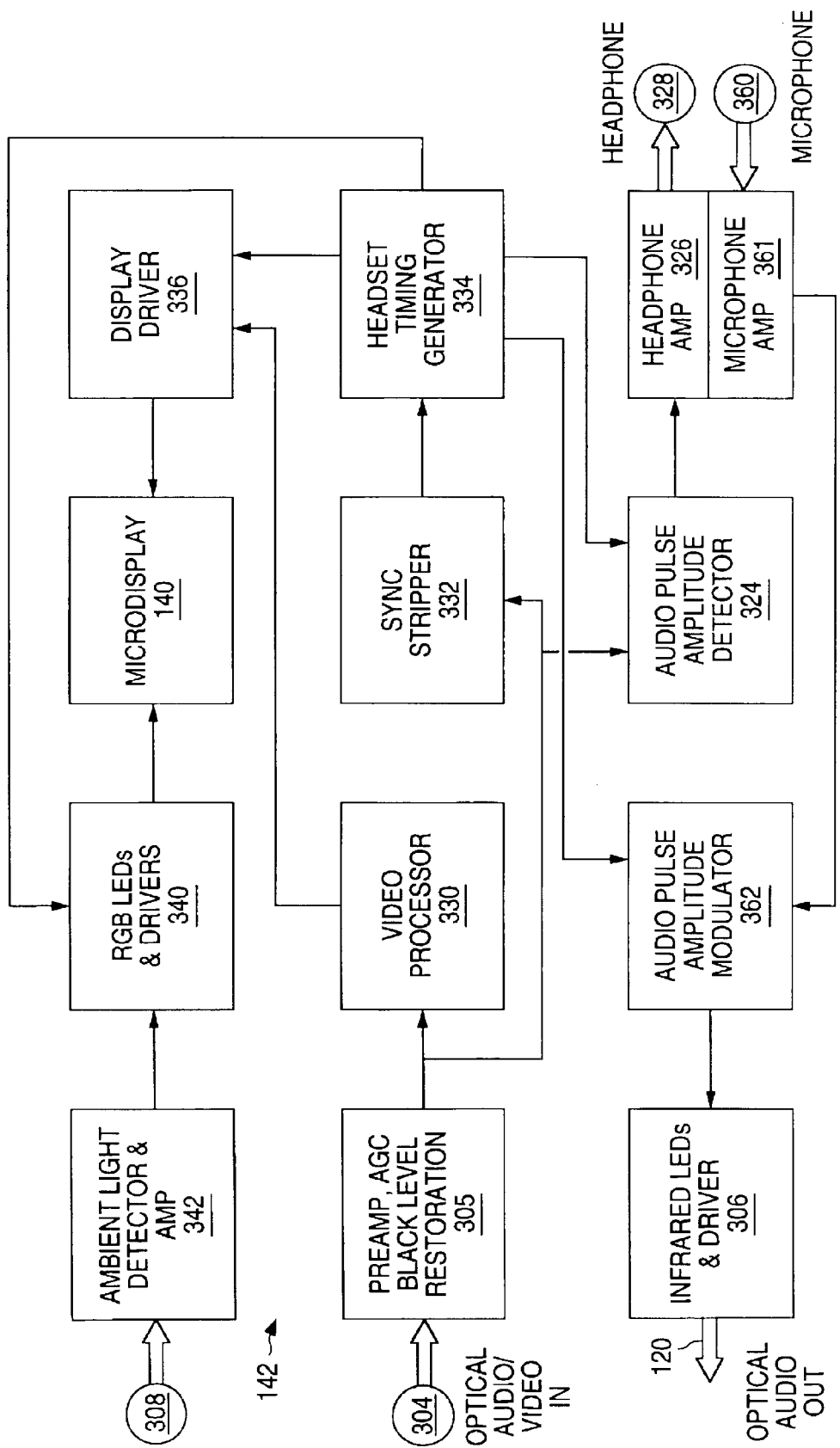
FIG. 3D is a functional block diagram of a remote electronics circuit, located for example at a headset.

FIG. 3D is a functional block diagram of remote electronic circuit 142, located for example at headset 104. The combined video and optional audio low level electronic signals from IR photodetector 304 enter adjacent to the middle left hand side of FIG. 3D. The signals are applied to preamplifier/AGC/audio carrier filter module 305 where the signal is amplified and level adjusted by a conventional automatic gain control (AGC) circuit. Black level control restores the correct baseline DC voltage to the video waveform.

The composite output from preamp module 305 is further separated into three 15 signals; a video signal portion by processor 330, synchronization components by stripper 332, and the optional audio component by detector 324. The synchronization components are applied to a headset timing generator 334, which generates signals that control display, LED illumination sub-systems, and optional audio subsystem.

The separated video signal portion continues into a video processing module 330, where gamma correction is performed using conventional techniques. Gamma correction compensates for the different response of headset display 140 relative to the response of a traditional phosphor based CRT. Gamma correction adjusts the video signal, such that headset display 140 exhibits a more accurate range of brightness than would be realized without gamma correction.

The optional audio carrier portion is separated from the video via pulse amplitude detector 324 (e.g., sample-and-hold) using reconstructed timing information from headset timing generator 334. The recovered audio signal is then applied to a headphone amplifier 326 configured for driving a conventional dynamic headphone speaker element 328.

Figure 3E:
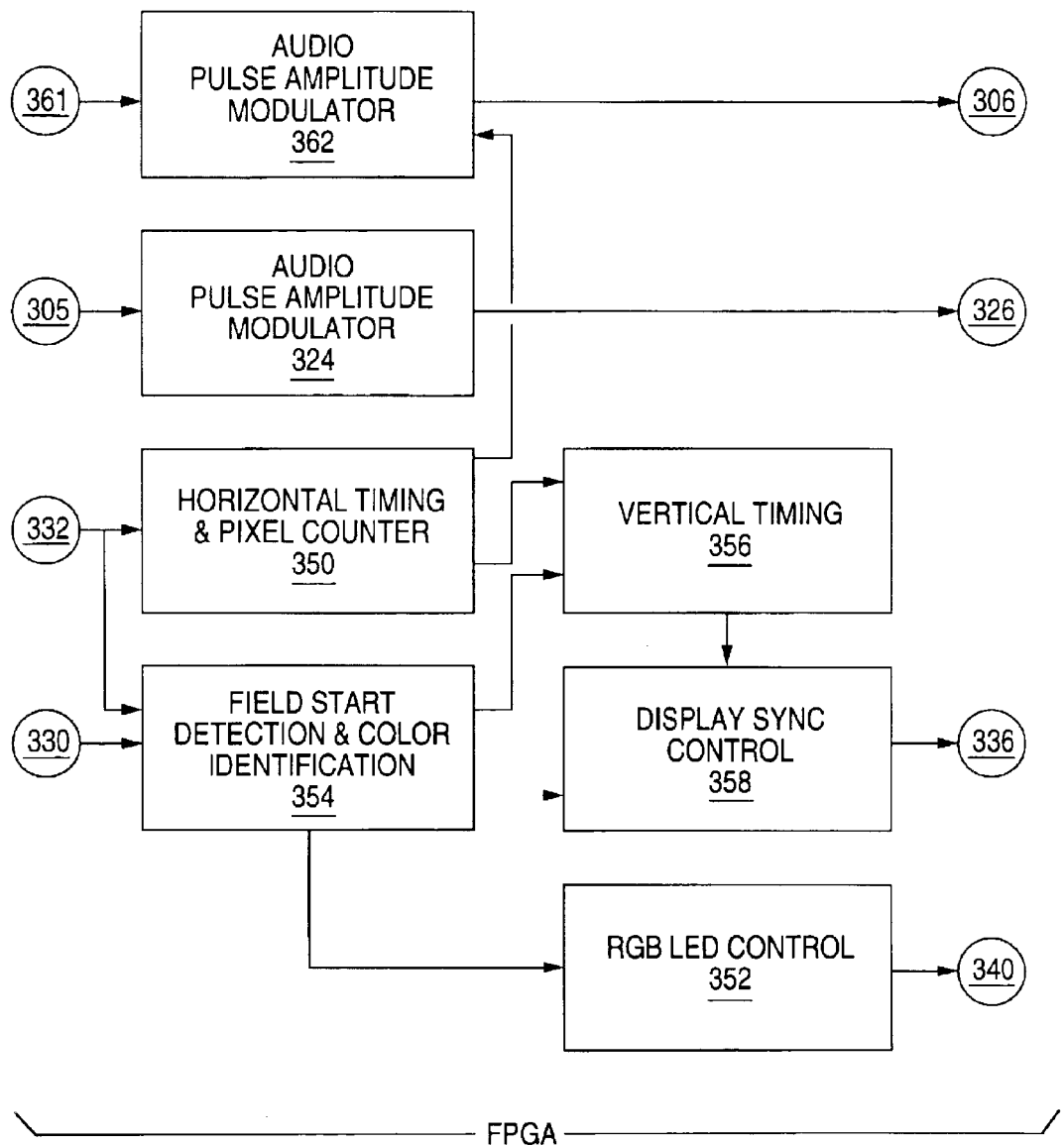
FIG. 3E is a detailed functional block diagram of a headset timing generator.

FIG. 3E is a detailed functional block diagram of headset timing generator 334, which is implemented with a field programmable gate array (FPGA), similar to that described in connection with FIG. 2A. The outputs from headset timing generator 334 include control signals for display drive module 336, display LEDs 340, and optional audio pulse separation. In operation, display 140 cycles through erase, load, and illuminate phases. Timing generator 334 is responsible for correctly sequencing these phases. Composite sync components from sync stripper module 332, including horizontal start pulses and field start pulses, are applied to headset timing generator 334. Using the. horizontal start pulses, a horizontal timer and pixel counter module 350 locates the beginnings of lines and counts the pixels within each line, for example, 800 active pixels per line of display 140 plus inactive pixels used for timing and control. A timing window is generated at the expected field start pulse time (with respect to the horizontal start pulse), that is used by field start detection and color identification module 354 to detect a start of field condition. When start of field is detected, a vertical timing module 356 is reset to zero and commences counting lines in a field, for example, 600 lines. During the vertical timing interval, a small number of non-video lines from video processor module 330 are encoded with color identifiers. These color identifiers are detected by field start detection and color identification module 354 and are used by a RGB LED control module 352 to synchronize display LEDs 340 with the appropriate color fields. Vertical timing pulses from vertical timing module 356 and color IDs from field start detection and color identification module 354 are used by display sync control module 358 to generate signals that control the operation of a display drive module 336 and microdisplay 140.

Display drive module 336 demultiplexes the video pixels, converting serial pixel analog voltages to parallel analog voltages suitable for driving a display. Microdisplay 140 and associated drivers 336 receive video data from video processor module 330 and control signals from headset timing generator 334. These are used to load the sequential color field data, which are stored in memory cells internal to microdisplay 140. After the data are loaded and stabilized, a selected red, green, or blue LED 340 is pulsed to illuminate display 140 with the correct color.

The overall brightness of display 140 is adjusted using an optional ambient light detector circuit 342. Light from the room is measured by a photodetector 308 to provide a control signal to boost or reduce the average brightness level of LEDs 340.

An optional return audio signal is generated by a microphone 360 mounted at headset 104, and is processed by audio electronics including a microphone amplifier 361 and an audio pulse amplitude modulator 362, in a manner similar to that described in connection with FIG. 2A. The processed return audio signal drives infrared LEDs 306, thereby generating modulated return IR beam 120, which is transmitted through the atmosphere to transceiver module 110, where it is collected and relayed to base station 112.

In an alternative return audio implementation, the return audio signal is digitized with a simple A/D converter within headset 104. It is then formatted, stored and restructured digitally by a PIC controller within timing generator 334 of FIG. 3D as a series of full-amplitude pulses occupying a time slot normally used for a full horizontal line of video; for example, every eighth line. The video normally occupying these lines is then blanked and delayed for IR transmission until the following lines, thereby adding 600/8 or 75 lines to the SVGA format. As with other timing functions, the video blanking and audio pulse formatting is controlled in base station 160 of FIG. 2A by generator 176 and synchronously controlled by headset timing generator 334 in FIG. 3D. Audio information is transmitted as an IR series of pulses in the same way by headset LEDs 306 in FIG. 3A, received by collecting lens and lightcone 252 in transceiver module 110, and sent through coaxial cable 151 in cable bundle 182 to base station 112, where it is digitally decoded and converted to analog audio for equivalent use. While this digital embodiment has the disadvantage of increasing the video bandwidth by 675 lines/600 lines, or 12.5%, it has the advantage of decreasing headset LED 306's power requirements for an equivalent S/N ratio to the pulse amplitude format; thereby extending the operational life of headset batteries 104.

Figure 4:
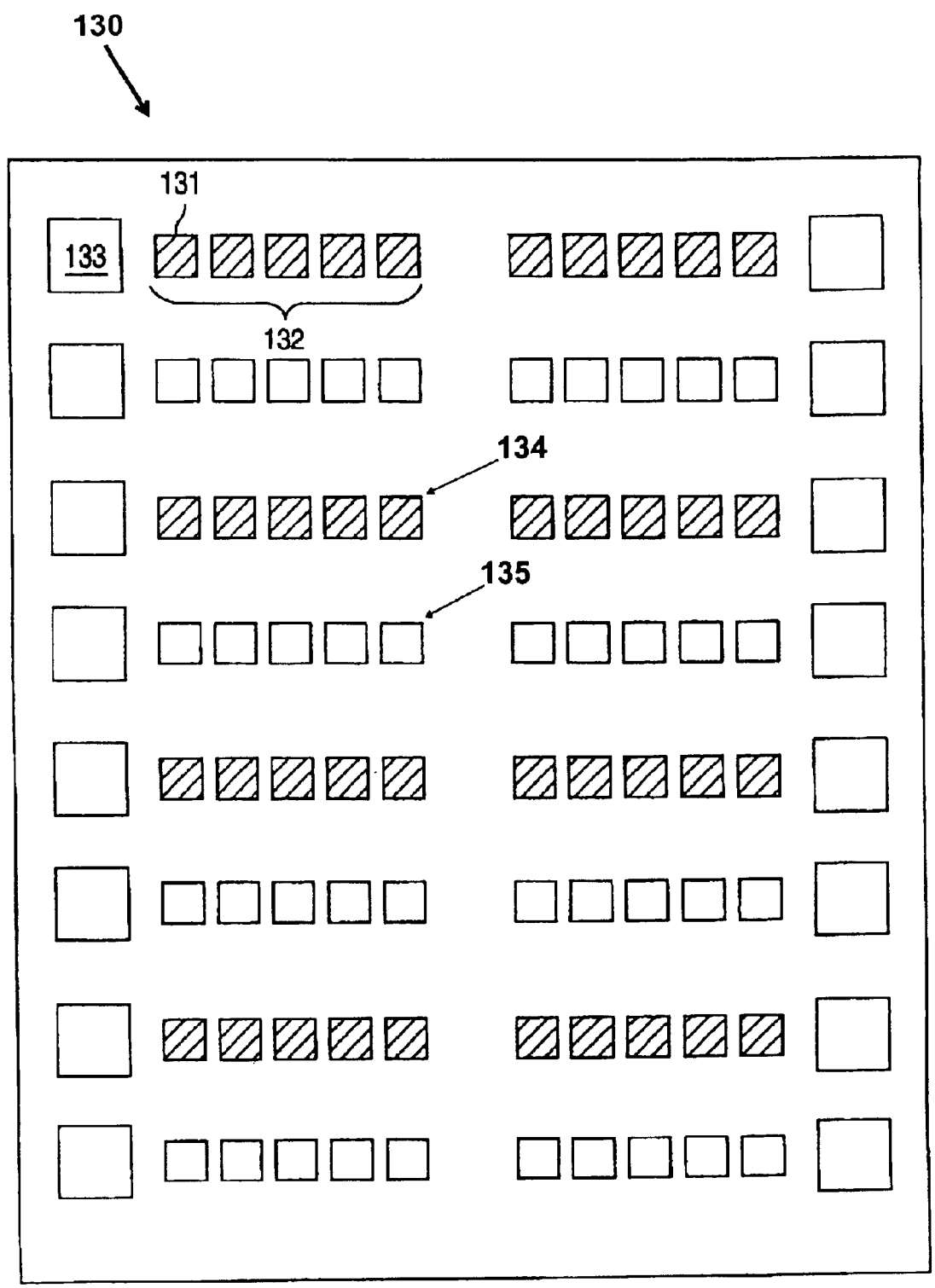
FIG. 4 is a schematic diagram of an array of IR LEDs.

FIG. 4 is a schematic diagram of LED array 130, in accordance with an embodiment of the present invention. FIG. 4 shows a cluster 132 of high-speed infrared-emitting LEDs 131 in the array with each LED 131 emitting an identical optical signal. FIG. 2D shows the LED array 130 is interconnected with the video processing circuit 160 in base station 112 through a single coaxial cable 182 or through one or more electrical cables 186.

In one embodiment, each cluster 132 consists of five LEDs 131 driven in series from a common modulated electrical source through electronic buffers 133 from a common +12 volt power supply 260 (FIG. 2C). The common modulated electrical source is electrical coaxial cable 182, as shown in FIG. 2D. Alternatively, the common modulated electrical source is a single coaxial cable 184 in bundle of cables 182, as in FIG. 2E. The clusters 132 of LEDs 131 and their common modulated electronic driver sources 133 are driven in parallel from the common modulated electrical source. This invention encompasses clusters with more than five LEDs and clusters with less than five LEDs. The optimum number of LEDs 131 in the array 130 depends on the desired minimum S/N ratio at the desired maximum range of separation between transceiver 110 and remote receiver 302. To those skilled in the art, it is generally understood that random noise from silicon detectors such as detector 304 in FIG. 3A is nearly constant, while signal strength generally falls off with the square of the range of separation. Therefore, doubling the number of LEDs 131 in array 130 will generally increase the S/N ratio by the square root of 2, or 44%, at a given range. Typically, the desired S/N ratio is reached at a ratio where an increase in the S/N ratio is no longer noticeable to the eyes of user 102. This is generally in excess 40 db.

In one embodiment, pairs of clusters 132 are physically arranged in an electronic dipole configuration so that the electromagnetic field from one cluster tends to cancel out the electromagnetic field from the other cluster. The cancellation of the electromagnetic fields minimizes spurious electronic emissions.

FIG. 4 shows a partially loaded circuit board with spaces i34 with loaded LEDs 131 and spaces 135 with unloaded LEDs. When the circuit board is partially loaded, the clusters 132 of LEDs 131 are symmetrically laid out as pairs of clusters so as to further minimize spurious electromagnetic radiation. Alternatively, the circuit board is fully loaded with LEDs 131. The spatially distributed nature of the array 130 minimizes the possibility of total blockage of the signal path to the headset 104 from an obstruction, such as a swinging arm of a surgical lighting system.

Figure 5I:
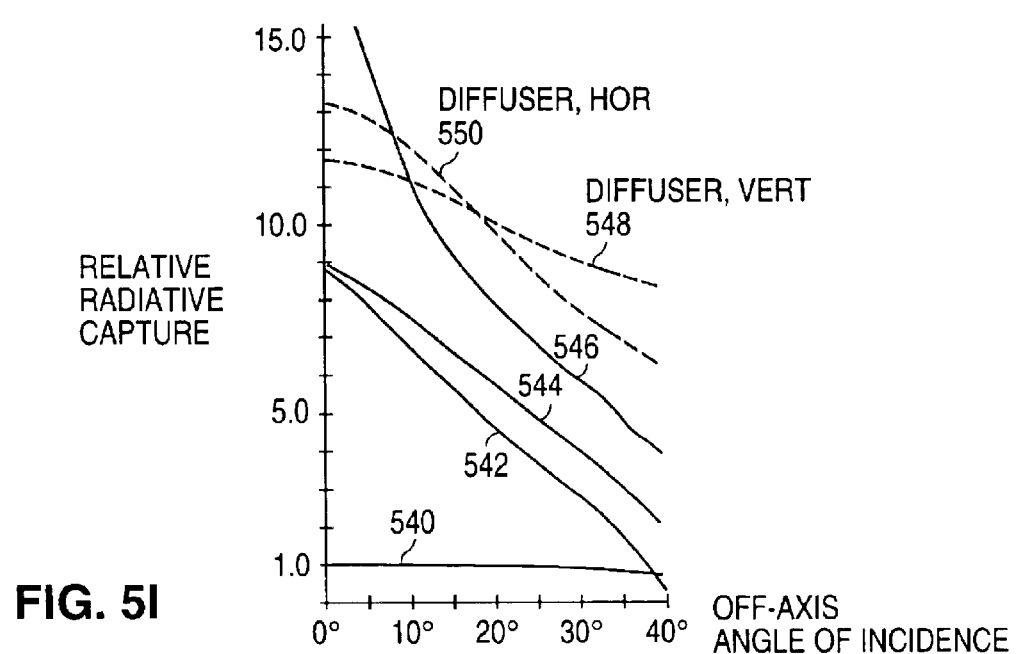
FIG. 5I is a graphic representation of the calculated radiative capture by various combinations of elements of the assembly of FIG. 5A, relative to the radiative capture by an unaided photodetector.
Figure 5A:
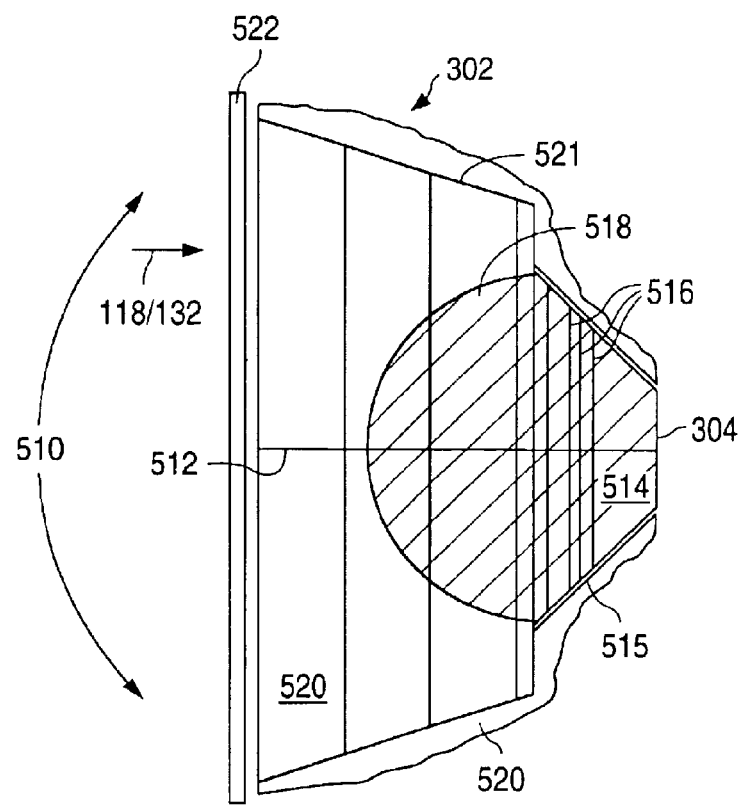
FIG. 5A is a cross-sectional schematic diagram of a collecting lens assembly, in accordance with an embodiment of the present invention.

FIG. 5A is a cross-sectional schematic diagram of collecting lens assembly 302 at headset 104, in accordance with an embodiment of the present invention. Collecting lens assembly 302 is configured to achieve both a large angular field of view 510, e.g., to accommodate head motion, and a large entrance pupil to receive maximum energy from IR signal 118 or 132. Although collecting lens assembly 302 is nominally rotationally symmetric about a symmetry axis 512, it can alternatively be configured to provide an azimuthally variable detectivity pattern about axis 512.

Photodetector 304 can be any photosensitive device having the optical and electronic responses required for the application, but is shown in FIG. 5A as a silicon device selected for its high frequency electronic performance and for high sensitivity to infrared radiation over a wavelength region of approximately 700 nm to approximately 1100 nm.

The collecting lens assembly 302 consists of three coaxial components: a refractive lens 518 with a conic sidewall and planar exit pupil, an inner cone 515 with a diffusely reflective sidewall mating to lens' 518 conic sidewall, and an outer cone 520 with smooth inner reflective walls extended above the lens which reflects IR signal 118 S or 132 into lens 518 and inner light cone 514 over a wider aperture. Inner walls 521 of outer cone 520 are oriented, for example, at an angle of approximately 19 degrees to approximately 27 degrees relative to symmetry axis 512. Photodetector 304 is optically cemented to the lens' 518 planar exit pupil to couple some energy into photodetector 304 that would otherwise be lost to total internal reflection within lens 518. This combination of elements dramatically enhances photodetector's 304 effective apperture over a wide angular field of view, thereby permitting the use of a smaller, wider bandwidth, less expensive photodetector to collect sufficient levels of infrared signal.

In some embodiments, one or more optical elements of the collecting lens assembly are aspheric. Collecting lens 518 has an aspheric first surface with a numerical aperture of approximately f/0.8, which provides a large entrance pupil. Transmissive optical elements are typically made from transparent polymeric material, for example polymethyl methacrylate, polycarbonate, and ULTEM® grade polycarbonate manufactured by General Electric Company. Reflective elements can be made of any material that is reflective in the infrared spectrum of interest; the preferred embodiment being a plastic such as polycarbonate that is reflectively overcoated with aluminum.

Collecting lens and light cone 252 has substantially the same structure as collecting lens assembly 302.

Figure 5B:
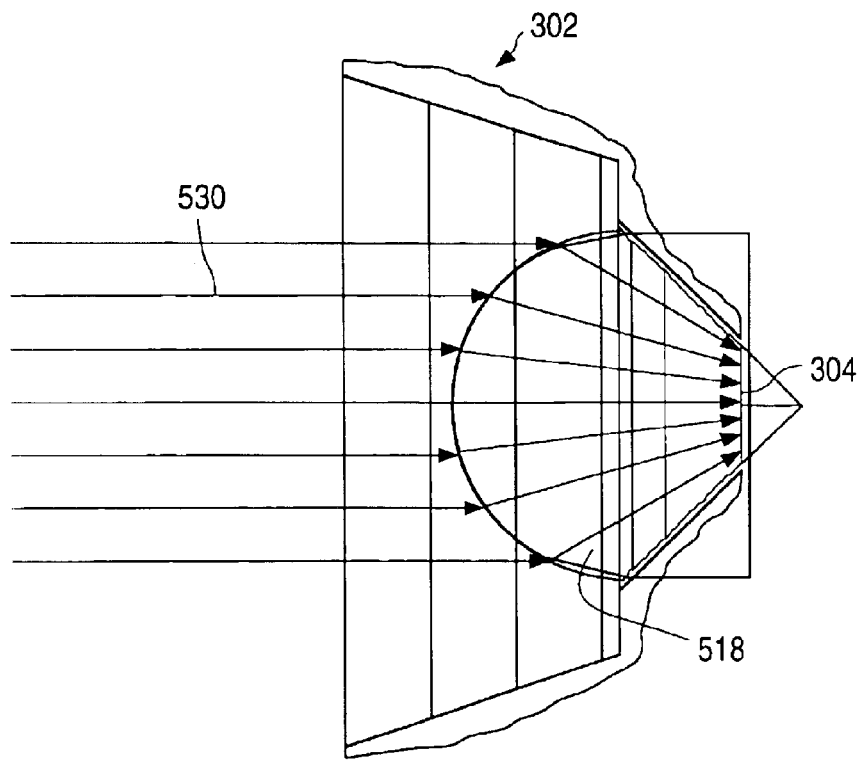
FIGS. 5B–5D are cross-sectional schematic diagrams illustrating the transmission and capture of IR radiation incident from various angles onto a collecting lens assembly.
Figure 5C:
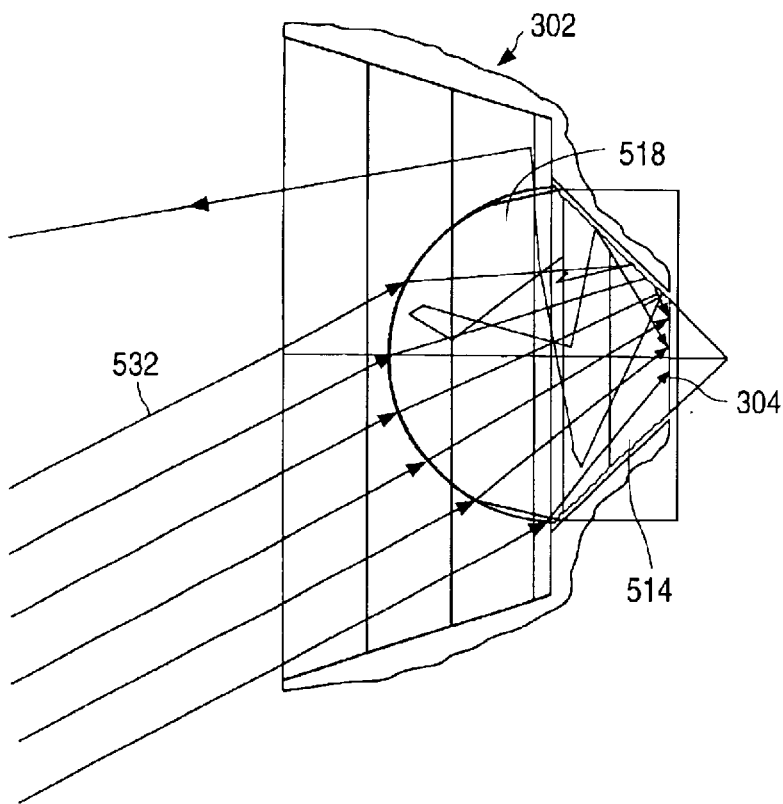
Figure 5D:
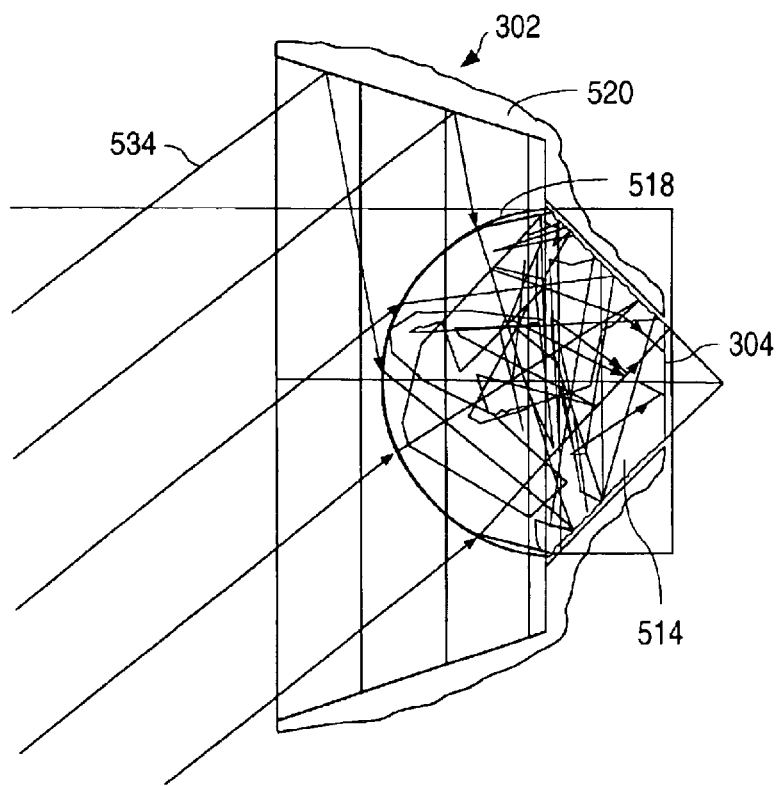

FIGS. 5B–5D are cross-sectional schematic diagrams illustrating the transmission and capture of IR radiation incident from various angles onto collecting lens assembly 302. FIG. 5B shows the case of radiation 530 incident normal to the plane of photodetector 304. This radiation is captured efficiently by wide-angle lens 518 alone. FIG. 5C shows the case of radiation 532 incident at a 30-degree angle from normal, which is efficiently captured by wide-angle lens 518 and inner light cone 514 cooperatively. FIG. 5D shows the case of radiation 534 incident at 40-degree angle from normal. In this situation, outer conic cavity 520 reflects radiation into wide-angle lens 518 that would otherwise be lost. This reclaimed radiation is then efficiently captured by wide-angle lens 518 and inner light cone 514 cooperatively.

Figure 5E:
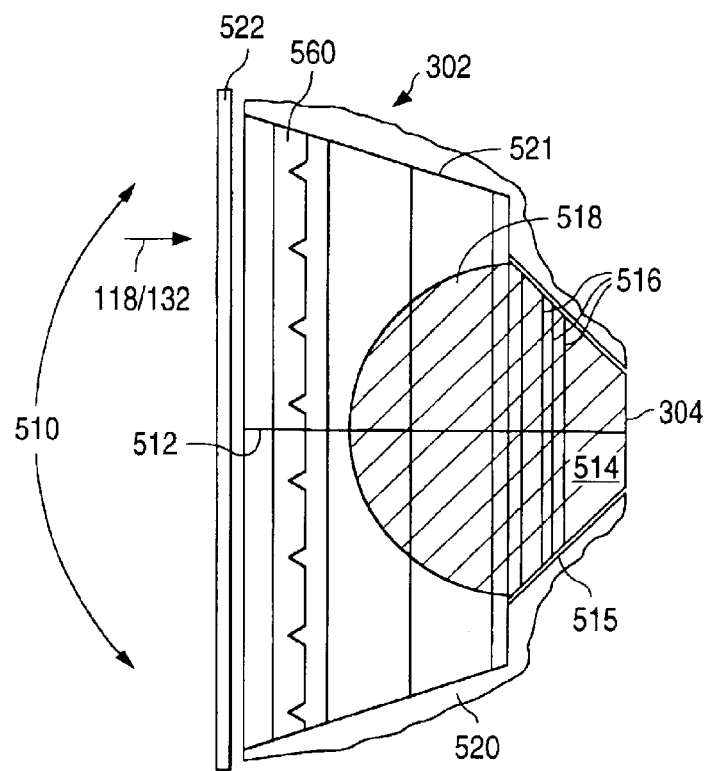
FIGS. 5E and 5F are cross-sectional schematic diagrams of a collecting lens assembly with a prismatic dispersion plate.
Figure 5F:
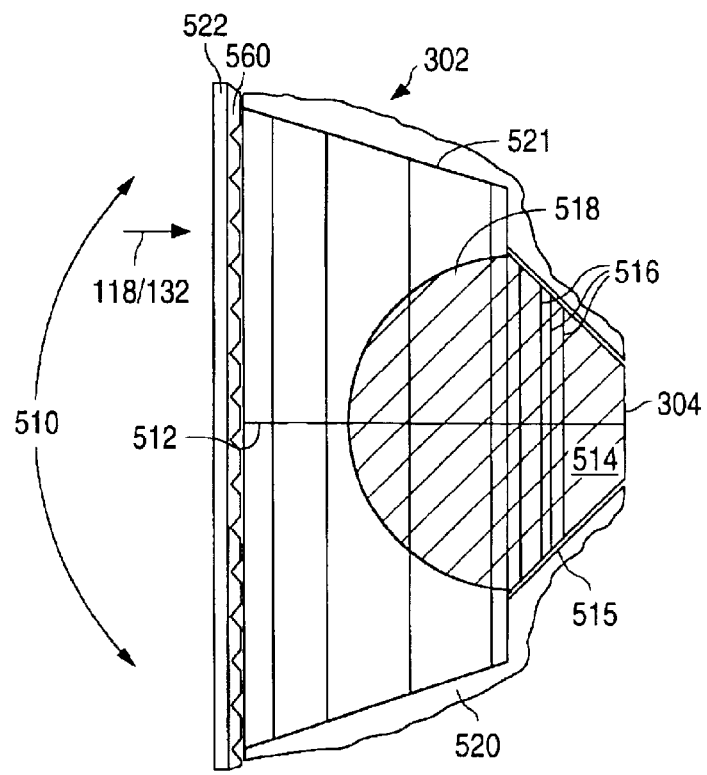

An optional prismatic dispersion plate overlying the outer conic cavity further widens the collecting angle of the assembly. FIGS. 5E and 5F are cross-sectional schematic diagrams of a collecting lens assembly 302 with prismatic dispersion plate 560. In one embodiment, the prismatic dispersion plate 560 overlies the outer conic cavity 520, as shown in FIG. 5E. Alternatively, the prismatic dispersion plate is molded together and integrated with the outer headset cover, an infrared pass filter window 522, as shown in FIG. 5F. The effect of this dispersion is further illustrated in FIG. 3C with the IR reception angle being widened from 80 degrees to 120 degrees, for example. The prismatic dispersion plate is typically made of an optically transmissive polymeric material (for example ULTEM®) grade polycarbonate manufactured by the General Electric Company).

Figure 5G:
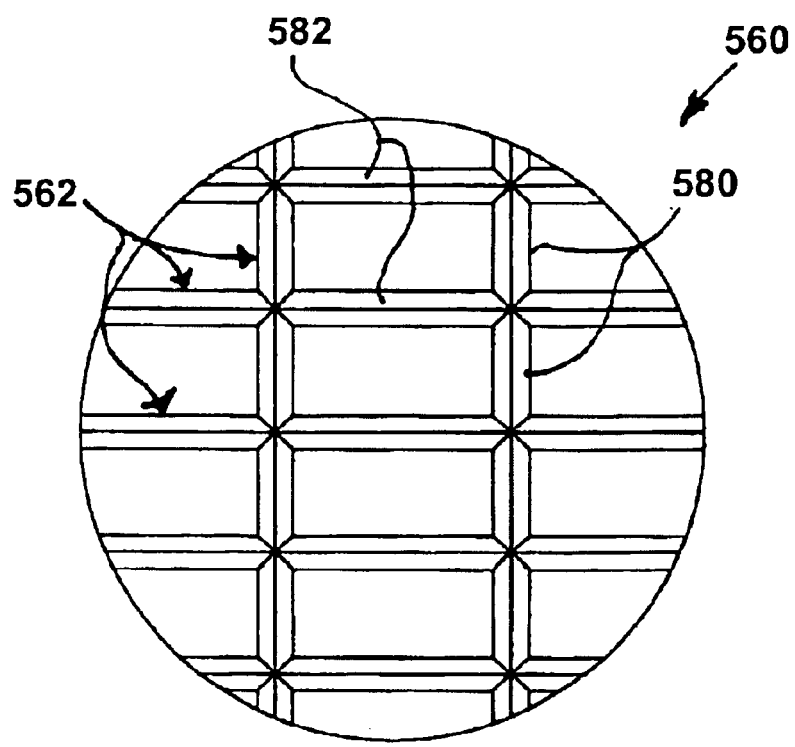
FIG. 5G is a plane view of a prismatic dispersion plate.

FIG. 5G is a plane view illustrating a prismatic dispersion plate 560. The grooves 562 widen the angular field of vision 510, or collection angle, of the collecting lens assembly. The plate 560 has both vertical 580 and horizontal 582 grooves. Horizontal grooves 582 widen the angular field of vision 510 during heads up-down motion, while vertical grooves 580 widen the angular field of vision 510 in side-to-side head motion. In one embodiment, the prismatic pattern is widened symmetrically with an equal number of horizontal grooves 582 and vertical grooves 580. Alternatively, the angular field of vision 510, or collection angle, is widened asymmetrically with an asymmetrical prismatic pattern. One embodiment has more horizontal grooves 582 than vertical grooves 580 to favor heads up-down motion over side-to-side head motion. Alternatively, side-to-side head motion is favored over heads up-down motion by having more vertical grooves 580 than horizontal qrooves 582.

Figure 5H:
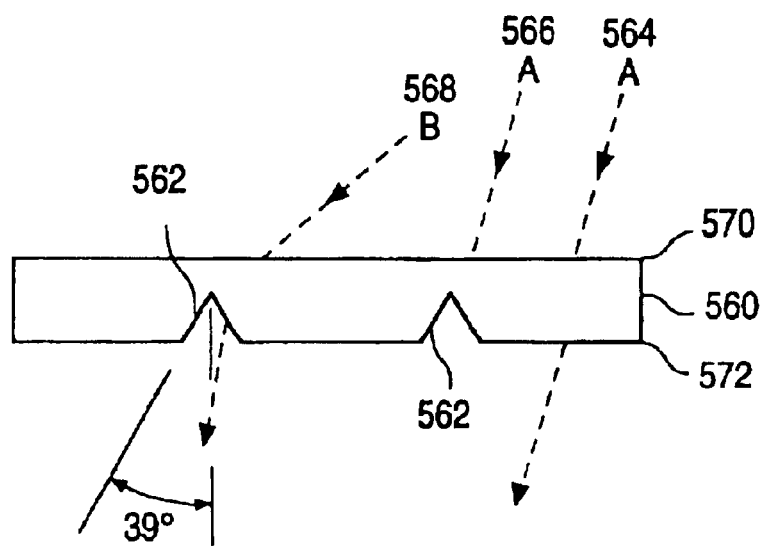
FIG. 5H is a cross-sectional schematic diagram illustrating the transmission and capture of IR radiation incident from various angles onto a prismatic dispersion plate.

FIG. 5H illustrates the transmission and capture of IR radiation incident from various angles onto the prismatic dispersion plate 560. IR rays 564 and 566 are within the normal angular range of the assembly ("on axis"), while IR ray 568 is an extreme angle outside the normal angular range of the assembly ("off axis"). On-axis JR ray 564 enters the prismatic dispersion plate 560 at surface 570 and is refracted slightly before exiting plate 560 at surface 572. On-axis IR ray 564 also enters the plate 560 at surface 570, but is internally reflected by groove 562, so it is does not reach the user 102. The grooves decrease on-axis sensitivity by internally reflecting some of the on-axis rays. However, the grooves enhance off-axis sensitivity. Off-axis IR ray 568 would normally not be within the angular range of the assembly. However, when an off-axis IR ray 568 enters the plate 560 at surface 570, the ray 568 is refracted by groove 562 to be within the angular acceptance of the collection lens assembly 302.

An optional optical bandpass filter is positioned over the assembly to minimize undesirable radiation (i.e., noise) outside of the infrared spectrum that constitutes the audio/video signal. An optical filter 522, such as KODAK WRATTEN® No. 87B, covers the entrance aperture of outer conic cavity 520. Alternatively, an optical filtering material such as an absorptive dye is incorporated into the material of wide-angle collecting lens 518 or dispersion plate 560.

FIG. 5I is a graphic representation of the calculated radiative capture by various elements of collecting lens assembly 302, relative to the radiative capture by photodetector 304 absent the other elements of collecting lens assembly 302. Relative radiative capture is shown along the vertical axis, and off-axis angle of incidence relative to symmetry axis 512 is shown along the horizontal axis. The baseline radiative capture of identically 1.0 by unaided photodetector 304 is shown as curve 540. Curve 542 shows the combined relative radiative capture by photodetector 304 and wide-angle collecting lens 518. Curve 544 shows the combined relative radiative capture by photodetector 304, wide-angle collecting lens 518, and inner light cone 514. Curve 546 shows the combined relative radiative capture by entire collecting lens assembly 302, including photodetector 304, wide-angle collecting lens 518, inner light cone 514, and outer conic cavity 520. As shown in FIG. 5I, the radiative capture by complete collecting lens assembly 302 relative to unaided photodetector 304 exceeds a factor of 15 on-axis and approximates a factor of four at a 40-degree angle off-axis. Curve 548 shows the relative radiative capture by the vertical grooves 580 in the prismatic dispersion plate 560. Curve 550 shows the relative radiative capture by the horizontal grooves 582 in the prismatic dispersion plate 560. The prismatic dispersion plate increases off-axis enhancement at the cost of on-axis sensitivity.

Referring to FIG. 1B, in an alternative embodiment, a tether 124 (shown dashed) is connected directly from base station 112 to remote electronic circuit 142 at headset 104, where it delivers the combined audio/visual signal. Tether 124 can contain either a single or dual optical fiber cable, such that a second optical fiber transmits return IR signal 120. Alternatively, tether 124 contains a bidirectional, electrically conducting coaxial cable. This configuration greatly simplifies IR video interface 100 by eliminating most components of transceiver module 110 and collecting lens assembly 302. The coaxial cable implementation additionally eliminates all optical and optoelectronic components. It also improves signal to noise performance at reduced power. However, the direct tether connection to headset 104 adversely restricts the freedom of motion of user 102.

Although a head-mounted display is described above, it will be understood by those having ordinary skill in the art that the principles, methods, and apparatus described herein can be applied as well to remote displays that are not head-mounted.

While embodiments of the present invention have been shown and described, changes and modifications to these illustrative embodiments can be made without departing from the present invention in its broader aspects. Thus it should be evident that there are other embodiments of this invention which, while not expressly described above, are within the scope of the present invention. Therefore, it will be understood that the appended claims necessarily encompass all such changes and modifications as fall within the described invention's true scope; and further that this scope is not limited merely to the illustrative embodiments presented to demonstrate that scope.

What is claimed is:

1. An apparatus including a video interface for a remote display, comprising:
   a video processing circuit configured to output a baseband video signal, said video signal having a data structure comprising a repetitive sequence of frame times, each said frame time containing substantially equal consecutive field times for each of three color fields;
   a transceiver module comprising a cluster of infrared light-emitting diodes coupled to said video processing circuit for transmitting said baseband video signal, and wherein the cluster includes a first group and a second group of light-emitting diodes that are arranged in an electronic dipole configuration such that the respective electromagnetic fields from the first and second groups cancel each other;
   a remote receiver configured to receive said baseband video signal; and
   a remote electronic circuit interconnected to said receiver and to a video display device, said remote electronic circuit configured to apply said baseband video signal to control and drive said video display device.

2. The apparatus of claim 1 wherein each diod in said cluster emits an identical optical signal.

3. The apparatus of claim 1 wherein said cluster further comprises at least a third group and a fourth group of said light-emitting diodes, said third and fourth groups being arranged in an electronic dipole configuration such that the respective electromagnetic fields from said third and fourth groups cancel each other.

4. The apparatus of claim 1 wherein said cluster of light emitting diodes is interconnected with said video processing circuit through electrical cables.

5. The apparatus of claim 1 wherein said cluster of light emitting diodes is interconnected with said video processing circuit through a coaxial cable.

6. The apparatus of claim 1 wherein said receiver comprises a collecting lens assembly comprising:
   a photodetector;
   an inner light cone optically coupled to said photodetector, said inner light cone having diffusely reflecting outer walls; and
   a wide-angle collecting lens coupled coaxially to said inner light cone.

7. The apparatus of claim 6 wherein said collecting lens assembly further comprises an outer conic cavity disposed coaxially around said wide angle collecting lens and inner light cone, said outer conic cavity having polished reflective inner walls.

8. The apparatus of claim 6 wherein said wide angle collecting lens is aspheric.

9. The apparatus of claim 6 wherein said collecting lens assembly comprises a prismatic dispersion plate for widening a collecting angle of said assembly.

10. The apparatus of claim 9 wherein said prismatic dispersion plate overlies said outer conic cavity.

11. The apparatus of claim 6 wherein said collecting lens assembly comprises an asymmetrical prismatic pattern for widening a collecting angle of said assembly asymmetrically.

12. The apparatus of claim 6 wherein said wide angle collecting lens and said inner light cone are an integrated monolithic structure.

13. The apparatus of claim 1 further comprising a headset to be worn by a user, said headset incorporating said receiver and said video display device.

14. The apparatus of claim 1 wherein said remote electronic circuit is configured to illuminate said video display device sequentially with light from colored light emitting diodes in synchronism with bursts of pixel luminance data, such that illumination occurs during a portion of each said field time not containing said burst.

15. The apparatus of claim 14 further configured to operate two separate video display devices alternately, such that data bursts of a first video signal for a first display device alternate with corresponding data bursts of a second video signal for a second display device, and wherein said first and second video signals are derived from a single time-duplexed video data stream.

16. The apparatus of claim 1 wherein said field time is in a range of approximately 4 msec to approximately 6 msec.

17. The apparatus of claim 1 further configured to provide a video bandwidth of the order of or greater than 100 MHz.

18. The apparatus of claim 1 wherein said video processing circuit is configured to convert a frame rate in an input video signal into a higher frame rate in said baseband video signal by repeated color fields.

19. The apparatus of claim 1 wherein said baseband video signal incorporates an embedded audio signal.

20. The apparatus of claim 1 further comprising a return audio link configured to propagate a return audio signal from the proximity of said remote receiver to the proximity of said video processing circuit.

21. An apparatus including a video interface for a remote display, comprising:
   a video processing circuit configured to output a baseband video signal;
   a remote receiver, said receiver configured to receive said baseband video signal;
   a remote electronic circuit interconnected between said receiver and a video display device, said remote electronic circuit configured to apply said baseband video signal to control and drive said video display device; and
   a transceiver module comprising a cluster of infrared light-emitting diodes located proximate to said receiver, wherein the cluster includes a first group and a second group of light-emitting diodes, the first and second groups being arranged in an electronic dipole configuration such that the respective electromagnetic fields from the first and second groups cancel each other, said transceiver module being configured to output said baseband video signal to said receiver at least in part through a free atmospheric path.

22. The apparatus of claim 21 wherein each diode in said cluster emits an identical optical signal.

23. The apparatus of claim 21 wherein each light-emitting diode in the cluster emits an identical optical signal.

24. The apparatus of claim 21 wherein said cluster further comprises at least a third group and a fourth group of said light-emitting diodes, said third and fourth groups being arranged in an electronic dipole configuration such that the respective electromagnetic fields from said third and fourth groups cancel each other.

25. The apparatus of claim 21 wherein said cluster of light emitting diodes is interconnected with said video processing circuit through electrical cables.

26. The apparatus of claim 21 wherein said cluster of light-emitting diodes is interconnected with said video processing circuit through a coaxial cable.

27. The apparatus of claim 21, wherein said receiver further comprises a collecting lens assembly incorporating:
   a photodetector;
   an inner light cone optically coupled to said photodetector, said inner light cone having diffusely reflecting outer walls; and
   a wide-angle collecting lens coupled coaxially to said inner light cone.

28. The apparatus of claim 27 wherein said collecting lens assembly further comprises an outer conic cavity disposed coaxially around said wide angle collecting lens and inner light cone, said outer conic cavity having polished reflective inner walls.

29. The apparatus of claim 28 wherein said wide angle collecting lens is aspheric.

30. The apparatus of claim 27 wherein said collecting lens assembly comprises a prismatic dispersion plate for widening a collecting angle of said assembly.

31. The apparatus of claim 30 wherein said prismatic dispersion plate overlies said outer conic cavity.

32. The apparatus of claim 27 wherein said collecting lens assembly comprises an asymmetrical prismatic pattern for widening a collecting angle of said assembly asymmetrically.

33. The apparatus of claim 21 further comprising a headset to be worn by a user, said headset including said receiver and said video display device.

34. The apparatus of claim 21 wherein said baseband video signal incorporates an embedded audio signal.

35. The apparatus of claim 21 further comprising a return audio link configured to propagate an audio signal from the proximity of said remote receiver to the proximity of said video processing circuit.

36. The apparatus of claim 21, wherein the baseband video signal is a serial data stream comprising a repeating sequence of three color fields.

37. The apparatus of claim 36, wherein at least some of the same color fields are repeated in said serial data stream.

38. An apparatus including a collecting lens assembly comprising:
   an inner light cone having diffusely reflecting outer walls;
   a wide-angle collecting lens coupled coaxially to said inner light cone;
   an outer conic cavity disposed coaxially around said wide-angle collecting lens, said outer conic cavity having polished reflective inner walls; and
   a prismatic dispersion plate for widening a collecting angle of said assembly.

39. The apparatus of claim 38 further comprising a headset configured to be worn by a user, said headset including said collecting lens assembly and a video display device.

40. The apparatus of claim 38 wherein said wide-angle collecting lens is made of an optically transmitting polymeric material.

41. The apparatus of claim 38 wherein said wide angle collecting lens and said inner light cone are an integrated monolithic structure.

42. The apparatus of claim 38, wherein the prismatic dispersion plate comprises an asymmetrical prismatic pattern.

43. A method of operating a remote video display device, comprising:
   generating a baseband video signal;
   transmitting said baseband video signal through a free atmospheric path to a remote receiver coupled to the remote video display device using a cluster of light-emitting diodes, and wherein the cluster includes a first group and a second group of light-emitting diodes that are arranged in an electronic dipole configuration such that the respective electromagnetic fields from the first and second groups cancel each other; and
   applying said baseband video signal to control and drive said remote video display device.

44. The method of claim 43 wherein said receiver comprises a collecting lens assembly incorporating:
   a photodetector;
   an inner light cone optically coupled to said photodetector, said inner light cone having diffusely reflecting outer walls; and
   a wide-angle collecting lens coupled coaxially to said inner light cone.

45. The method of claim 44 wherein said collecting lens assembly further comprises an outer conic cavity disposed coaxially around said wide angle collecting lens and inner light cone, said outer conic cavity having polished reflective inner walls.

46. The method of claim 44 wherein said wide angle collecting lens is aspheric.

47. The method of claim 44 wherein said collecting lens assembly comprises a prismatic dispersion plate for widening a collecting angle of said assembly.

48. The method of claim 44 wherein said prismatic dispersion plate overlies said outer conic cavity.

49. The method of claim 44 wherein said collecting lens assembly comprises an asymmetrical prismatic pattern for widening a collecting angle of said assembly asymmetrically.

50. The method of claim 43 wherein said receiver and said video display device are incorporated in a headset worn by a user.

51. The method of claim 43 further comprising embedding an audio signal in said baseband video signal.

52. The method of claim 43 further comprising transmitting a return audio signal from the proximity of said remote receiver.

* * * * *